United States Patent
Lange et al.

(10) Patent No.: US 6,768,920 B2
(45) Date of Patent: Jul. 27, 2004

(54) SYSTEM FOR DELIVERING PAIN-REDUCTION MEDICATION

(75) Inventors: Daniel H. Lange, Kfar Vradim (IL); Reuven Lewinsky, Caesarea (IL)

(73) Assignee: Algodyne, Ltd., Ramat Hasharon (IL)

(*) Notice: Subject to any disclaimer, the term of this patent is extended or adjusted under 35 U.S.C. 154(b) by 0 days.

(21) Appl. No.: 09/977,448

(22) Filed: Oct. 12, 2001

(65) Prior Publication Data

US 2002/0128567 A1 Sep. 12, 2002

Related U.S. Application Data

(63) Continuation of application No. 09/899,824, filed on Jul. 5, 2001.
(60) Provisional application No. 60/216,464, filed on Jul. 6, 2000, and provisional application No. 60/241,722, filed on Oct. 18, 2000.

(51) Int. Cl.$^7$ ................................................. A61B 5/04
(52) U.S. Cl. ....................... 600/545; 600/300; 600/544; 604/65; 604/66; 604/67; 604/503
(58) Field of Search ............... 604/65–67, 890.1–897.1, 604/512; 600/514–545, 300–301

(56) References Cited

U.S. PATENT DOCUMENTS

| | | | |
|---|---|---|---|
| 4,430,074 A | * 2/1984 | Mooring | 604/506 |
| 4,667,513 A | 5/1987 | Konno | |
| 4,697,599 A | 10/1987 | Woodley et al. | |
| 4,844,091 A | 7/1989 | Bellak | |
| 4,871,351 A | * 10/1989 | Feingold | 604/66 |
| 5,018,526 A | 5/1991 | Gaston-Johansson | |
| 5,041,086 A | * 8/1991 | Koenig et al. | 604/65 |
| 5,069,218 A | 12/1991 | Ikeda | |
| 5,092,343 A | 3/1992 | Spitzer et al. | |
| 5,150,323 A | 9/1992 | Castelaz | |
| 5,207,642 A | * 5/1993 | Orkin et al. | 604/65 |
| 5,242,406 A | * 9/1993 | Gross et al. | 604/132 |
| 5,402,520 A | 3/1995 | Schnitta | |
| 5,415,641 A | * 5/1995 | Yerlikaya et al. | 604/251 |
| 5,445,622 A | * 8/1995 | Brown | 604/25 |
| 5,533,514 A | 7/1996 | Lavigne et al. | |
| 5,617,513 A | 4/1997 | Schnitta | |
| 5,634,472 A | 6/1997 | Raghuprasad | |

(List continued on next page.)

FOREIGN PATENT DOCUMENTS

| | | |
|---|---|---|
| DE | 30 04 126 A1 | 8/1981 |
| JP | 7023964 | 1/1995 |
| WO | WO 98/16152 | 4/1998 |

OTHER PUBLICATIONS

M. Abeles, Y. Prut, E. Vaadia, and A. Aertsen, "Integration, synchronicity and periodicity," in *Brain Theory: Spatio–Temporal Aspects of Brain Function*, A. Aertsen Ed., Elsevier Science Publishers B.V., 1993, pp. 149–181.

H. Akaike, "Statistical predictor identification," *Ann. Inst. Stat. Math.*, vol. 22, pp. 203–217. 1970.

J.I. Aunon, C.D. McGillem, and D.G. Childers, "Signal processing in evoked potential research: averaging and modeling," CRC *Crit. Rev. Bioeng.*, vol. 5, pp. 323–367, 1981.

(List continued on next page.)

*Primary Examiner*—Charles Marmor
*Assistant Examiner*—Patricia C. Mallari
(74) *Attorney, Agent, or Firm*—Jones Day

(57) ABSTRACT

Methods, apparatuses and systems relating to the objective measurement of the subjective perception of pain in a subject are disclosed. In one aspect, a system for objectively measuring a subjective perception of pain by a subject comprises a plurality of electrodes, including a left channel electrode and a right channel electrode. The plurality of electrodes measures electrical activity at a respective plurality of sites on the subject to generate at least two sets of electrical activity measurements. The system further comprises a processor for processing the at least two sets of electrical activity measurements into at least two normalized signals, and comparing the at least two normalized signals to each other to identify the presence of pain in the subject.

3 Claims, 9 Drawing Sheets

U.S. PATENT DOCUMENTS

| | | | |
|---|---|---|---|
| 5,643,302 A | * 7/1997 | Beiser et al. | 606/167 |
| 5,687,291 A | 11/1997 | Smyth | |
| 5,692,500 A | 12/1997 | Gaston-Johansson | |
| 5,742,694 A | 4/1998 | Eatwell | |
| 5,846,208 A | 12/1998 | Pichlmayr et al. | |
| 5,873,900 A | 2/1999 | Maurer et al. | |
| 5,878,389 A | 3/1999 | Hermansky et al. | |
| 5,916,172 A | 6/1999 | Hodges et al. | |
| 5,941,833 A | 8/1999 | Lipman | |
| 5,995,868 A | 11/1999 | Dormeister et al. | |
| 6,016,444 A | * 1/2000 | John | 600/544 |
| 6,018,675 A | * 1/2000 | Apkarian et al. | 600/407 |
| 6,044,303 A | 3/2000 | Agarwala et al. | |
| 6,047,202 A | 4/2000 | Finneran et al. | |
| 6,049,727 A | * 4/2000 | Crothall | 600/410 |
| 6,067,567 A | 5/2000 | Bartfai et al. | |
| 6,105,015 A | 8/2000 | Nguyen et al. | |
| 6,113,552 A | 9/2000 | Shimazu et al. | |
| 6,128,346 A | 10/2000 | Suarez et al. | |
| 6,146,334 A | 11/2000 | Laserow | |
| 6,168,569 B1 | 1/2001 | McEwen et al. | |
| 6,464,687 B1 | * 10/2002 | Ishikawa et al. | 604/89.1 |
| 6,558,351 B1 | * 5/2003 | Steil et al. | 604/131 |

OTHER PUBLICATIONS

E.A. Bartnik, K.J. Blinowska, and P.J. Durka, "Single evoked potential reconstruction by means of wavelet transform," *Biol. Cybern.*, vol. 67, pp. 175–181, 1992.

H.A. Beagly, B.M. Sayers, and A.J. Ross, Fully objective ERA by phase spectral analysis, *Acta Otolaryngol*, vol. 87, pp. 270–278, 1979.

G.E. Birch, P.D. Lawrence, and R.D. Hare, "Single–trial processing of event related potentials using outlier information," *IEEE Trans. Biomed. Eng.*, vol. 40, pp. 59–73, 1993.

G.E.P. Box and G.M. Jenkins, *Time series analysis: forecasting and control*. San Francisco, CA: Holden–Day, 1976.

E.H. Carlton and S. Katz, "Is wiener filtering an effective method of improving evoked potential estimation ?," *IEEE Trans. Biomed. Eng.*, vol. 34, No. 1, 1987.

S. Cerutti, G. Baselli, G. Pavesi, "Single sweep analysis of visual evoked potentials through a model of parametric identification," *Biol. Cybernetics*, vol. 56, pp. 111–120, 1987.

S. Cerutti, G. Chiarenza, D. Liberati, D. Liberati, P. Mascellani, and G. Pavesi, "A parametric method of identification of single trial event related potentials in the brain," *IEEE Trans. Biomed. Eng.*, vol. 35, pp. 701–711, 1988.

K.H. Chiappa, *Evoked potentials in clinical medicine*. New York: Raven, 1983.

V.H. Clarson and J.J. Liang, "Mathematical classification of evoked potential waveforms," *IEEE Trans. Sys. Man & Cybern.*, vol. 19, pp. 68–73, 1989.

A.M. Dale and M.I. Sereno, "Improving localization of cortical activity by combining EEG and MEG with MRI cortical surface reconstruction: a linear approach," *Journal of Cognitive Neuroscience*, vol. 5, 162–176, 1993.

J.P.C. de Weerd, "A posteriori time–varying filtering of averaged evoked potentials. I. Introduction and conceptual basis," *Biol. Cybernetics.*, vol. 41, pp. 211–222, 1981.

L. Deecke, B. Grozinger, and H.H. Kornhuber, "Voluntary finger movement in man: cerebral potentials and theory," *Biol. Cybernetics*, vol. 23, pp. 99–119, 1976.

E. Donchin, "A Multivariate approach to the analysis of average evoked potentials," *IEEE. Trans. Biomed. Eng.*, vol. 13, pp. 131–139, 1966.

E. Donchin and E. Heffley, "Multivariate analysis of event–related potential data: a tutorial review," in *Multidisciplinary perspectives in event–related brain potential research*, D. Otto (Ed.), Washington D.C.: Government Printing Office, pp. 555–572, Dec. 1978.

D.J. Doyle, "Some comments on the use of wiener filtering in the estimation of evoked potentials," *Electroencephalogr. Clin. Neurophysiol.*, vol. 28, pp. 533–534, 1975.

R.O. Duda and P.E. Hart, Pattern *classification and scene analysis*. Wiley: New–York, 1976.

L.A. Farwell and E. Donchin, "Taking off the top of your head: toward a mental prosthesis utilyzing event–related potentials," *Electroencephalogr. Clin. Neurophysiol.*, vol. 70, pp. 510–523, 1988.

L.A. Farwell and E. Donchin, "The truth will out: Interrogative polygraphy with event related brain potentials," *Psychophysiology*, vol. 28, 1991.

J.A. Freeman and D.M. Skapura. *Neural networks: Algorithms, applications, and programming techniques*: Addison–Wesley Publishing Company, USA, pp. 531–547, 1992.

M. Furst and A. Blau, "Optimal a–posteriori time domain filter for average evoked potentials," *IEEE Trans. Biomed. Eng.*, vol. 38, pp. 827–833, 1991.

W. Gersch, "Spectral analysis of EEG's by autoregressive decomposition of time series," *Math. Biosc.* vol. 7, pp. 205–222, 1970.

A.S. Gevins, "Analysis of the electromagnetic signals of the human brain: milestones, obstacles and goals," *IEEE Trans. Biomed. Eng.*, vol. 31, pp. 833–850, 1984.

A.S. Gevins, N.H. Morgan, S.L. Bressler, J.C. Doyle, and B.A. Cutillo, "Improved event related potential estimation using statistical pattern classification," *Electroencephalogr. Clin. Neurophysiol.*, vol. 64, pp. 177–186, 1986.

G.H. Golub and C.F. Van Loan, *Matrix computations*. Johns Hopkins University Press, Balti–more, MD, 1983.

L. Gupta, D. L. Molfese, R. Tammana, and P. G. Simos, "Nonlinear alignment and averaging for estimating the evoked potential," *IEEE Trans. Biomed. Eng.*, vol. 43, pp. 348–356, 1996.

S. Haykin, *Adaptive filter theory*. Prentice–Hall: N.J., 1986.

S. Haykin. *Neural Networks: A Comprehensive Foundation*: Macmillan College Publishing Company, Inc., USA, 1994.

J. Hertz, A.. Krogh, and R.G. Palmer. *Introduction to the theory of neural computation*. Addison–Wesley Publishing Company, USA, 1991.

H.H. Jasper, "The ten–twenty electrode system of the international federation," *Electroenc. Clin. Neurophysiol.*, vol. 10, pp. 371–375, 1958.

J.P. Kaipio and P.A. Karjalainen, "Estimation of event related synchronization changes by a new tvar method," *IEEE Trans. Biomed. Eng.*, vol. 44, pp. 649–656, 1997.

X. Kong and N.V. Thakor, "Adaptive Estimation of Latency Changes in Evoked Potentials," *IEEE Trans. Biomed. Eng.*, vol. 43, pp. 189–197, 1996.

R. Kristeva, D. Cheyne, W. Lang, G. Lindinger, and L. Deecke, "Movement related potentials accompanying unilateral and bilateral finger movements with different inertial loads," *Electroencephalogr. Clin. Neurophysiol.*, vol. 75, pp. 410–418, 1979.

R. Kristeva, E. Keller, L. Deecke and H.H. Kornhuber, "Cerebral potentials preceding unilateral and bilateral simultaneous finger movement," *Electroencephalogr. Clin. Neurophysiol.*, vol. 47, pp. 229–238, 1979.

P. Laguna, R. Jane', O. Meste, P.W. Poon, P. Caminal, H. Rix, and N.V. Thakor, "Adaptive filter for event–related bioelectric signals using an impulse correlated reference input: comparison with signal averaging techniques," *IEEE Trans. Biomed. Eng.*, vol. 39, pp. 1032–1043, 1992.

D.H. Lange, H. Pratt, and G.F. Inbar, "Segmented matched filtering of singe event related evoked potentials," *IEEE Trans. Biomed. Eng.*, vol. 42, pp. 317–321, 1995.

D.H. Lange and G.F. Inbar, "A robust parametric estimator for single–trial movement related brain potentials," *IEEE Trans. Biomed. Eng.*, vol. 43, pp. 341–347, 1996.

D.H. Lange and G.F. Inbar. "Parametric modeling and estimation of amplitude and time shifts in single evoked potential components". in *Advances in Processing and Pattern Analysis of Biological Signals*, L Gath and G. F. Inbar, Eds. Plenum Press: 1996.

D.H. Lange and G.F. Inbar, "Brain–wave based polygraphy," in *Proc. IEEE EMBS96*, Amsterdam, 1996.

D.H. Lange, H. Pratt, and G.F. Inbar, "Modeling and estimation of single evoked brain potential components," *IEEE Trans. Blomed. Eng.*, vol. 44, pp. 791–799, 1997.

D.H. Lange, H.T. Siegelman, H. Pratt, and G.F. Inbar, "A generic approach for identification of event related brain potentials via a competitive neural network structure," to appear in Proc. NIPS*7—*Neural Information and Processing Systems: Natural & Synthetic*, 1998.

D. Liberati, S. DiCorrado, and S. Mandelli, "Topographic mapping of single sweep evoked potentials in the brain," *IEEE Trans. Biomed. Eng.*, vol. 39, pp. 943–951, 1992.

P.G. Madhaven, "Minimal repetition evoked potential by modified adaptive line enhancement," *IEEE Trans. Biomed. Eng.*, vol. 39, pp. 760–764, 1992.

J. Makhoul, "Linear prediction: a tutorial review," *Proc. IEEE*, vol. 63, pp. 561–580, 1975.

S.G. Mason, G.E. Birch, and M.R. Ito, "Improved single–trial signal extraction of low SNR events," *IEEE Trans. Sig. Proc.*, vol. 42, pp. 423–426, 1994.

G. McCarthy and E. Donchin, "A Metric for Thought: A Comparison of $P_{300}$ Latency and Reaction Time," *Science*, vol. 211, pp. 77–80 , 1981.

H.J. Michalewski, D.K. Prasher, and A. Starr, "Latency variability and temporal interrelationships of the auditory event–related potentials (N1,P2,N2, and P3) in normal subjects," *Electroenc. Clin. Neurophysiol.*, vol. 65, pp. 59–71, 1986.

O. Meste and H. Rix, "Jitter statistics estimation in alignment processes," *Signal Processing*, vol. 51, pp. 41–53, 1996.

J.M. Moser and J.I. Aunon, "Classification and detection of single evoked brain potentials using time–frequency amplitude features," *IEEE Trans. Biomed. Eng*, vol. 33, pp. 1096–1106, 1986.

M. Nakamura, "Waveform estimation from noisy signals with variable signal delay using bispectrum averaging," *IEEE Trans. Biomed. Eng.*, vol. 40, pp. 118–127, 1993.

P.L. Nunez, *Electric fields of the brain*. Oxford University Press, 1981.

T.W. Picton and S.A. Hillyard, "Endogenous event related potentials," in *Handbook of electroencephalographic clinical neurophysiology*, vol. 3, T. W. Picton, Ed. Amsterdam: Elsevier, 1988, pp. 361–426.

D. Popivanov and I. Krekule, "Estimation of homogenity of a set of evoked potentials with respect to its dispersion," *Electroencephalogr. Cln. Neurophysiol*, vol. 55. pp. 606–608, 1983.

H. Pratt, H.J. Michalewski, G. Barrett, and A. Starr, "Brain potentials in memory–scanning task: modality and task effects on potentials to the probes," *Electroencephalogr. Cln. Neuro physiol.*, vol. 72, pp. 407–421, 1989.

M.A. Rodriguez, R.H. Williams, and T.J. Carlow, "Signal delay and waveform estimation using unwarpped phase averaging," *IEEE Trans. Acoust. Sp. & Sig. Proc.*, vol. 29, pp. 508–513, 1981.

O. Rompelman and H.H. Ros, "Coherent averaging technique: a tutorial review. Part 1: Noise reduction and the equivalent filter," *J. Biomed. Eng.*, vol. 8, pp. 24–29, 1986.

O. Rompelman and H.H. Ros, "Coherent averaging technique: a tutorial review. Part 2 Trigger jitter, overlapping responses and non–periodic stimulation" J. Biomed. Eng., vol. 8 pp. 30–35, 1986.

A.V. Rotterdam., "Limitations and difficulties in signal processing by means of the principal component analysis," *IEEE Trans. Biomed. Eng.*, vol. 17, pp. 268–269, 1970.

D.E. Rumelhart and D. Zipser, "Feature discovery by competitive learning," *Cognitive Science* vol. 9, pp. 75–112, 1985.

V.L. Schwent and S.A. Hillyard, "Evoked potential correlates of selective attention with multi channel auditory inputs," *Electroencephalogr. Clin. Neurophysiol.*, vol. 38, pp. 131–138, 1975.

M.V. Spreckelsen and B. Bromm, "Estimation of single–e-voked cerebral potentials by means o parametric modeling and kalman filtering," *IEEE Trans. Biomed. Eng.*, vol. 35, pp. 691–700 1988.

O. Svensson, "Tracking of changes in latency and amplitude of the evoked potential by using adaptive LMS filters and exponential averagers," *IEEE Trans. Biomed. Eng.*, vol. 40, pp 1074–1079, 1993.

N.V. Thakor, "Adaptive filtering of evoked potentials," *IEEE Trans. Biomed. Eng.* , vol. 34 pp. 6–12, 1987.

N.V. Thakor, X.R. Guo, C.A. Vaz, P. Laguna, R. Jane, P. Caminal, H. Rix, and D.F. Hanley "Orthonormal (Fourier and Walsh) models of time varying evoked potentials in neurologic injury," *IEEE Trans. Biomed. Eng.* , vol. 40, pp. 213–221, 1993.

H.G. Vaughan, Jr. and J.C. Arezzo, "The neural basis of event related potentials," in Handbook of *Electroenceph. and Clin. Neurophysiol.*, vol. 3, T.W. Picton Ed., Amsterdam: Elsevier 1998 pp. 45–87.

R.S. Varga, *A decomposition technique for signals overlapping in time*. Ph.D. Dissertation University of Florida, 1969.

C.A. Vaz and N.V. Thakor, Adaptive fourier estimation of time–Varying evoked potentials, *IEEE Trans. Biomed–Eng.*, vol. 3, pp. 448–455, 1989.

R. Verleger and E. Wascher, "Fitting ex–Gauss functions to P3 waveshapes: an attempt distinguishing between real and apparent changes of P3 latency," *Journal of Psychophysiology* vol. 9, pp. 146–158, 1995.

D.O. Walter, "A posteriori wiener filtering of average evoked responses," *Electroencephalog Clin. Neurophysiol.*, suppl., vol. 27, pp. 61–70, 1969.

C.D. Woody, "Characterization of an adaptive filter for the analysis of variable latency neuroelectric signals," *Med. & Biol. Eng.*, vol. 5, pp. 539–5531 1967.

K. Yu and C.D. McGillem, "Optimum filters for estimating evoked potential waveforms," *IEEE Trans. Biomed. Eng.*, vol. 30, pp. 730–737, 1983.

Feng, X.; Schulteis, J., *Identification Of high noise lime series signals using hybrid ARMA modeling and neural network approach*, Neural Networks, 1993., IEEE International Conference on, Mar. 28–Apr. 1, 1993, Page(s): 1780–1785, vol. 3.

Mitra, S.; Pemmaraju, S., *Efficient coding by neuro–fuzzy clustering in vector quantization of wavelet decomposed signals*, Fuzzy Information Processing Society, 1996. NAFIPS., 1996 Biennial Conference of the North American, Jun. 19–22, 1996, Page(s): 229–233.

Ming–Yao Yang; Wei–Chih Hu; Liang–Yu Shyu, *ECG Events Defection and Classification Using Wavelet and Neural Networks*, Engineering in Medicine and Biology Society, 1997. Proceedings of the 19th Annual International Conference of the IEEE vol.: 1, Oct. 30–Nov. 2, 1997, Page(s):280–281.

Hara, K.; Nakayama, K., *Classification Of Multi–frequency Signals With Random Noise Using Multileyr Neural Networks*, Neural Networks, Oct. 25–29, 1993. IJCNN '93–Nagoya. Proceedings of 1993 International Joint Conference on, vol: 1, Page(s): 601–604.

Schnaufer, B.A.; Jenkins, W.K., *Adaptive fault tolerance for reliable LMS adaptive filtering*, Circuits and Systems II: Analog and Digital Signal Processing, IEEE Transactions on, vol: 44 Dec. 12, 1997, Page(s): 1001–1014.

W.W.L. Keerthipala; Low Tah Chong; Tham Chong Leong, *Artificial neural network model for analysis of power system harmonics*, Neural Networks, 1995. Proceedings., IEEE International Conference on, vol.: 2, Nov. 27–Dec. 1, 1995, Page(s): 905–910 vol. 2.

Hara, T.—Itoh, A.; Yatsuka, K.; Kishi, K.; Hirotsu, K., *Application of the neural network to detecting corona discharge occurring in power cables*, Neural Networks to Power Systems, 1993. ANNPS'93., Proceedings of the Second International Forum on Applications of, Apr. 19–22, 1993, Page(s): 259–264.

Buhmann, J.M.; Hofmann, T., *Robust vector quantization by competitive learning*, Acoustics, Speech, and Signal Processing, 1997. ICASSP–97., 1997 IEEE International Conference on, vol: 1, Apr. 21–24, 1997, Page(s): 139–142 vol. 1.

Manjunath, B.S.; Chellappa, R., *A unified approach to boundary perception: edges, textures, and illusory contours*, Neural Networks, IEEE Transactions on, vol.: 4 Jan. 1, 1993, Page(s): 96–108.

* cited by examiner

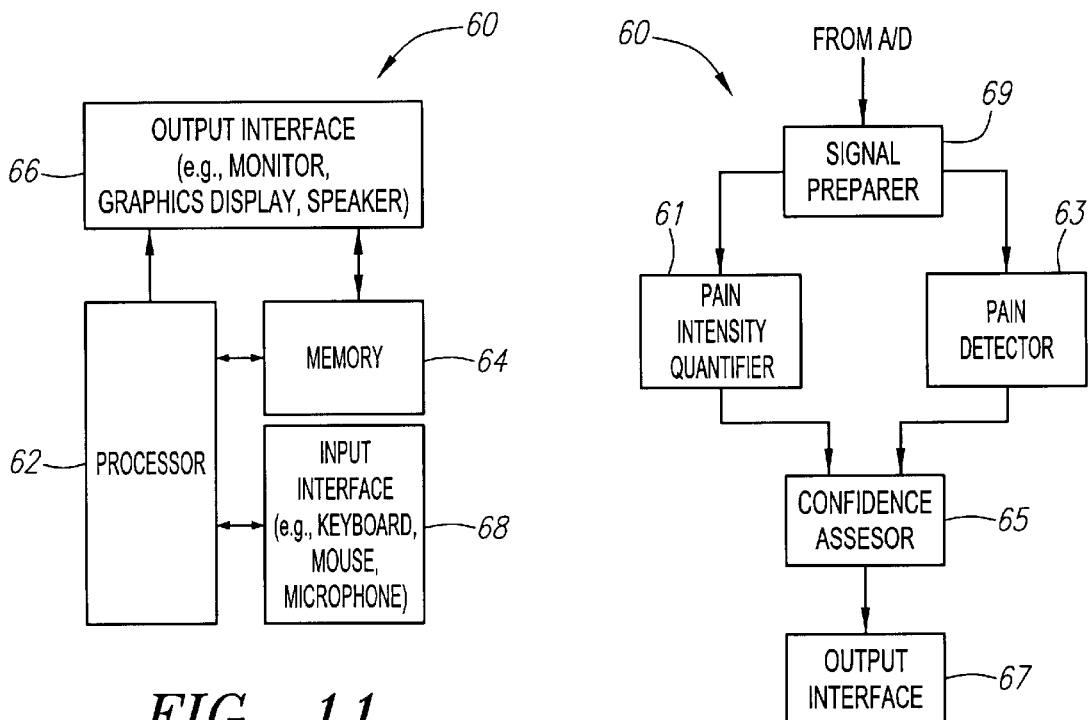
*FIG. 11*
*FIG. 12*
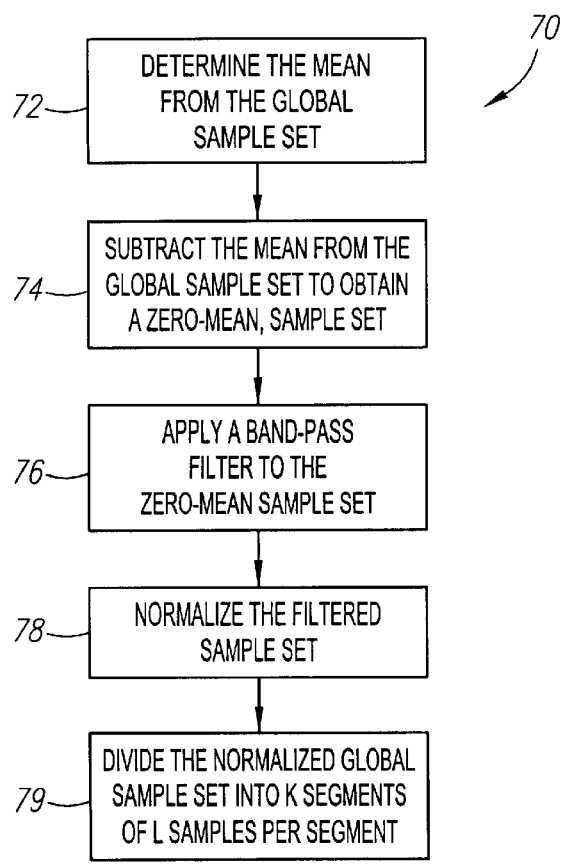
*FIG. 13*
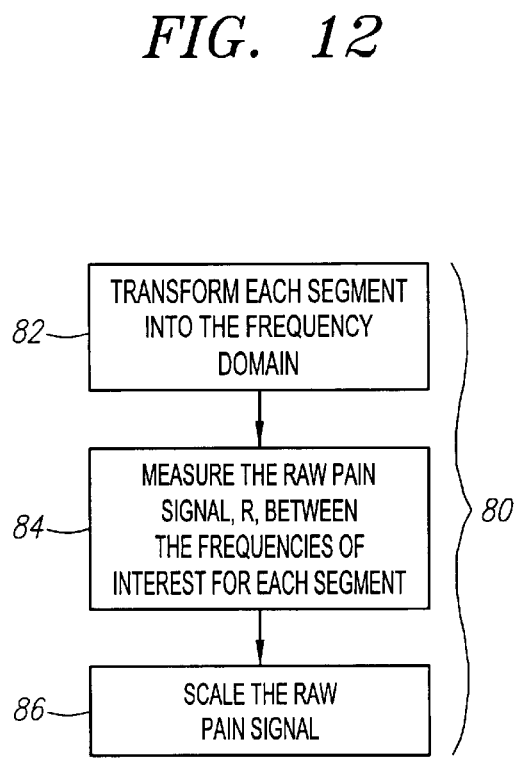
*FIG. 14*

SYSTEM FOR DELIVERING PAIN-REDUCTION MEDICATION

This application is a continuation application of U.S. patent application Ser. No. 09/899,824, filed on Jul. 5, 2001, entitled "Objective Pain Measurement System And Method", which claims priority to U.S. Provisional application No. 60/216,464 filed on Jul. 6, 2000 and to U.S. Provisional application No. 60/241,722 filed on Oct. 18, 2000.

BACKGROUND OF THE INVENTION

1. Field of the Invention

The field of the present invention relates to medical diagnostic tools. More particularly, the field of the present invention relates to systems and methods relating to measuring and reporting a subject's pain.

2. Background

Pain is an unpleasant sensation, ranging from slight discomfort to intense suffering. But because to a great extent pain is a subjective phenomenon, it has frequently defied objective, quantitative measurement. Traditionally, physicians have had to assess a patient's pain by relying on the patient's own description of it. But self-description is not only subjective by definition, it is often inaccurate, in part because it is difficult for subjects to precisely articulate their pain while in the midst of a pain experience.

Moreover, objective assessment of pain is all but impossible in situations where the patient is not fully communicative, such as when the patient is an infant, the patient is not fully conscious or coherent, or the patient is a non-human.

Today, uni-dimensional scales are used to quantify pain. These scales frequently employ verbal (mild, moderate, severe) and numerical (0–10) ratings. Today's caregivers also use multidimensional scales along with complex, pain diagnosis questionnaires designed to extract as much subjective information as possible from the subject (e.g. sensory, emotional and cognitive).

These pain quantification methods are used in a number of settings. Most commonly, physicians and other health care professionals apply these methods to diagnose and/or treat a patient. Physicians may also use these methods to track the progress of a patient's illness over time or to determine an amount of pain medication to prescribe to a patient. In other settings, these methods are used to test the efficacy of certain pain-relieving drugs and to establish standard dosages for them. Nonetheless, these methods often lead to inaccurate conclusions because of the subjective nature of the assessment inherent in them.

Logically, pain assessment plays a vital role in determining the amount of pain medication to give a patient. As a result, hospital staff and other health care providers also use visual clues to assess the intensity of a patient's pain and determine the amount of pain medication to provide. Under this visual assessment method, the caregiver will commonly use a visual analog scale (VAS), usually scored from 1 to 10, to rate a patient's pain intensity. In a typical scenario, the caregiver will consider different clues to score the patient's pain intensity, such as facial expressions and cardio-respiratory function, in addition to patient statements of satisfaction.

Notwithstanding the healthcare providers' diligence, studies have shown that professional caregivers usually give too much or too little pain medication to patients evaluated with these visual scoring methods. Importantly, a caregiver's failure to give enough pain medication may not only reduce a patient's quality of life, but may compromise a patient's ability to fight disease, cause or complicate physiological disorders, and even hasten death. On the other hand, caregivers that overmedicate patients can also cause harmful side effects, including, in extreme cases, patient respiratory arrest.

Some patients also intentionally misrepresent the existence or extent of their pain. These misrepresentations may stem from financial or fiduciary incentives (including a desire for disability payments or insurance damage settlements), chemical dependencies on pain medications, or other patient-perceived secondary benefits to obtaining pain medication. Regardless of the motivation, patient misrepresentation accounts for a significant portion of the demand for pain medication prescriptions. Yet, without any reliable basis for denying such prescriptions, physicians generally must assume that the claims are truthful, even when they may suspect a lack of sincerity. Otherwise, the caregiver may be accused of inhumane treatment. Conversely, other patients may underreport their pain, again for a variety of reasons.

Despite these inaccurate representations, hospitals and other healthcare givers often provide patients with a class of devices known as Patient Controlled Analgesia (PCA) devices. PCA devices employ a type of analgesia system that enables the patient, often in a post-operative setting, to self-administer pain medicine.

Commercial PCA devices include devices such as the Atom PCA Pump 500, APII, Deltec CADD-PCA 5800, Sabratek 6060 and the Verifuse. In a common form of PCA, the patient is provided with a mechanical apparatus comprised of a reservoir and a patient-operable pump. On patient demand, the pump dispenses incremental doses of pain medicine from the resevoir into the patient's intravenous (IV) system. The device may also comprise a lock-out interval feature that prevents patient remediation for a period of time so as to ensure against over-medication.

While caregivers using VAS methods cannot consistently provide the right amount of pain medication to patients, studies have likewise shown that a patient's own assessment of satisfaction, even when used in connection with a PCA device, does not reliably indicate when to deliver pain medication. One study shows that although patients may feel satisfied by a regimen of self-administered pain therapy, the majority of those same patients are self-treated below their individual subjective pain thresholds. Forst et. al., Archives of Orthopaedic and Trauma Surgery (Germany), v. 119, p. 267–270, (1999). Moreover, the act of self-medication itself has been found to be unimportant to the issue of patient satisfaction when the patient has sufficient pain relief through medication. Chumbley, et al., Anesthesia (England), v. 54 (4), p. 386–9 (1999).

The present PCA methods and systems also have other drawbacks. For example, they cannot be readily used, if at all, for infants, toddlers, certain spinal cord patients, and others who cannot operate the device or are unable to understand the instructions for controlling the PCA. Also, current PCA devices do not normalize people's responses, thereby making the subjective nature of pain self-assessment a factor in the operation of the PCA. Even in honest attempts to be objective, patients may rate the same subjective experience of pain differently. For example, one person may rate a certain subjective sensation of pain a "10" on the VAS scale whereas another person may rate the same or a similar subjective sensation of pain a "5" depending on a variety of psychological factors and life experiences. Thus, without a means to normalize patient self-assessment, PCA devices rely on subjective psychological factors as much as on the type of illness to determine how much pain medicine to provide.

Moreover, self-assesment may lead to inconsistent treatment between different patient types. For example, children who use PCA devices have been reported to frequently experience nausea and vomiting as a result of overdoses, as compared with adults. PCA devices also do not typically reduce the burden on caregivers because, in many cases, the caregivers must repeatedly instruct patients on how to use the PCA devices and monitor their use.

In contrast, previous efforts in pain research have attempted to identify physiological phenomena related to the subjective sensation of pain. Heart-rate, blood pressure, perspiration and skin conductance are some of the physiological phenomena that have been found to be affected by pain. But these physiological phenomena have also been found to be non-specific to pain and, in fact, have been used in other applications, such as polygraphy. Furthermore, these physiological phenomena tend to habituate quickly. Consequently, they are inadequate for objectively assessing pain.

U.S. Pat. No. 6,018,675 issued to Apkarian et al. discloses a pain measurement system based on comparative functional magnetic resonance imaging (MRI) of the brain of a subject. In the disclosed system, measurements quantifying a subject's pain level are made by comparing images of the subject's brain when the subject is in pain with the corresponding brain images made when the subject is not in pain. The system therefore generally requires a baseline, pain-free brain image for each subject. Furthermore, the functional MRI-based measurement system is generally a large piece of machinery, is not portable and requires a substantial infrastructure, including trained personnel to operate.

SUMMARY OF THE INVENTION

The present invention provides, in one aspect, systems and methods for objectively assessing a subject's subjective perception of pain.

In a second separate aspect, the present invention is a system comprising a plurality of sensors for measuring electrical activity at a respective plurality of sites on the subject in order to generate a set of electrical activity measurements. The system further comprises a processor for processing the set of electrical activity measurements into a normalized signal, and determining a level value representative of an objective pain measurement for the normalized signal within a predetermined range of frequencies.

In a third separate aspect, the present invention comprises a specific method of objectively measuring a level of pain subjectively perceived by a subject. The method preferably includes the steps of selecting a plurality of sites on the subject for sensing electrical activity, making electrical activity measurements for the plurality of sites, processing the electrical activity measurements into a normalized signal, and determining a level value for the normalized signal within a predetermined range of frequencies.

In a fourth separate aspect, the present invention comprises a computer-readable medium on which are stored sequences of instructions for objectively measuring a subjective perception of pain in a subject. The sequences of instructions are for performing the steps in the method of the third aspect identified above.

In a fifth separate aspect, the present invention is a system comprising means for measuring a subject's electrical activity at a plurality of sites in order to generate a set of electrical activity measurements. The system further includes processing means for processing the set of electrical activity measurements into a normalized signal, determining a level value for the normalized signal within a predetermined range of frequencies, and scaling the value for the signal into an objective pain measurement.

In a sixth separate aspect, the present invention is a system comprising a plurality of sensors, including a left channel electrode and a right channel electrode. The plurality of sensors measures a subject's electrical activity at a respective plurality of sites in order to generate at least two sets of electrical activity measurements. The system further comprises a processor for processing the at least two sets of electrical activity measurements into at least two normalized signals, and comparing the at least two normalized signals to each other in order to identify the presence of pain in the subject.

In a seventh separate aspect, the present invention comprises a specific method of objectively measuring a level of pain subjectively perceived by a subject. The method preferably includes the steps of selecting a plurality of sites on the subject for sensing electrical activity, making electrical activity measurements for the plurality of sites, processing the electrical activity measurements into at least two normalized signals, and comparing the at least two normalized signals to each other in order to identify the presence of pain in the subject.

In an eighth separate aspect, the present invention comprises a computer-readable medium on which are stored sequences of instructions for objectively measuring a subjective perception of pain in a subject. The sequences of instructions are for performing the steps in the method of the seventh aspect identified above.

In a ninth separate aspect, the present invention is a system comprising means for measuring a subject's electrical activity at a respective plurality of sites in order to generate at least two sets of electrical activity measurements. The system further comprises means for processing the at least two sets of electrical activity measurements into at least two normalized signals, and comparing the at least two normalized signals to each other in order to identify the presence of pain in the subject.

In a tenth separate aspect, the present invention comprises a network for objectively measuring pain subjectively perceived by one or more subjects. The network preferably includes at least one signal acquisition subsystem for making electrical activity measurements at a site on each of the one or more subjects, a signal processing subsystem for analyzing the electrical activity measurements and determining analysis values representing different periods of time, and a communication channel linking the signal processing subsystem and the at least one signal acquisition subsystem in order to transmit the subjects' electrical activity measurements to the signal processing subsystem.

In an eleventh separate aspect, the present invention comprises a pain measurement report comprising a reference to a subject and a value or series of values representing an objective level of pain subjectively experienced by the subject.

In a twelfth separate aspect, the present invention comprises a method of operating a network based on the analysis of pain-related electrical activity measurements. The method preferably comprises the steps of receiving electrical activity measurements on a subject from a testing location, analyzing the electrical activity measurements to obtain an objective pain measurement report, transmitting the objective pain measurement report to the testing location, and receiving non-medical patient information, including, for example, the number of reports, insurance information, incurred costs, patient contact information, patient histories, and patient feedback.

In a thirteenth separate aspect, the present invention comprises an acquisition system for acquiring an objective signal representative of a subjective perception of pain experienced by a subject. The acquisition system preferably comprises a sensor array for measuring an electrical signal at a site on the subject, an amplifier for amplifying the signal, and a band-pass filter for substantially removing components of the signal below about 0.1 Hertz and above about 5 Hertz.

In a fourteenth separate aspect, the present invention comprises a method of acquiring a signal representative of a subjective perception of pain experienced by a subject. The method preferably includes the steps of detecting an electrical signal at a site on the subject, amplifying the signal, and filtering the signal to substantially remove components of the signal below about 0.1 Hertz and above about 5 Hertz.

In a fifteenth separate aspect, the present invention comprises a system for processing electrical activity measurements taken from a subject. The system comprises a memory for storing the electrical activity measurements and a processor for processing the electrical activity measurements into a normalized signal. A processor is also provided to determine a level value for the normalized signal within a predetermined range of frequencies and to scale the level value for the signal into an objective pain level.

In a sixteenth separate aspect, the present invention comprises a specific method of processing electrical activity measurements taken from a subject. The method comprises the steps of processing the electrical activity measurements into a normalized signal, determining a level value for the normalized signal within a predetermined range of frequencies, and scaling the level value for the signal into an objective pain measurement.

In a seventeenth separate aspect, the present invention comprises a sensor array for measuring electrical activity on the forehead of a subject. The sensor array preferably includes a sensor pad, a left channel electrode positioned proximal to a left edge of the sensor pad, a right channel electrode positioned proximate to a right edge of the sensor pad, a common electrode positioned equidistant from the left channel electrode and the right channel electrode, and filtering circuitry electrically connected to the electrodes in order to filter signals from the electrodes in the range of about 0.1 Hertz to about 5 Hertz.

In an eighteenth separate aspect, the present invention comprises a physiological monitor for measuring multiple physiological signs of a subject. The physiological monitor preferably comprises a system for objectively measuring a subjective perception of pain, in combination with any one or more of a thermometer, a pulse meter, a blood pressure gauge and a respiratory gauge.

In a nineteenth separate aspect, the present invention is a system for delivering medication for reducing pain in a subject. The system preferably comprises a reservoir for containing the medication, a delivery device connected to the reservoir for delivering the medication to the subject, a delivery counter (connected to the reservoir) for measuring the amount of medication transferred between the reservoir and the delivery device, and an objective pain measurement device for objectively measuring a subjective perception of pain experienced by the subject. The system preferably further includes a medication delivery controller in communication with the objective pain measurement device, the delivery counter and the delivery device. The medication delivery controller preferably controls the amount of medication delivered to the subject by the delivery device based on a delivery rate communicated by the delivery counter and an objective pain measurement communicated by the objective pain measurement device.

In a twentieth separate aspect, the present invention is an electrical signal containing information objectively describing an intensity of a subjective experience of pain in a subject. The electrical signal is obtained by a process comprising the steps of selecting a site on the subject for sensing electrical activity, detecting electrical activity from the site, and filtering the electrical activity within a frequency range of about 0.1 Hertz to about 5 Hertz.

The foregoing methods may be implemented in the form of systems, devices, and computer-readable media. Further embodiments as well as modifications, variations and enhancements of the invention are also described herein.

BRIEF DESCRIPTION OF THE DRAWINGS

FIG. 11 is a block diagram illustrating one hardware configuration of a signal processing subsystem, such as that generally depicted in FIG. 1.

FIG. 12 is a functional block diagram illustrating one preferred embodiment of a signal processing subsystem, such as that generally depicted in FIG. 1.

FIG. 13 is a process flow diagram illustrating one embodiment of a signal preparation method, such as may be performed by the signal preparer represented in FIG. 12.

FIG. 14 is a process flow diagram illustrating one embodiment of a pain intensity quantification method, such as may be performed by the pain intensity quantifier represented in FIG. 12.

DETAILED DESCRIPTION OF THE PREFERRED EMBODIMENTS

Figure 1:
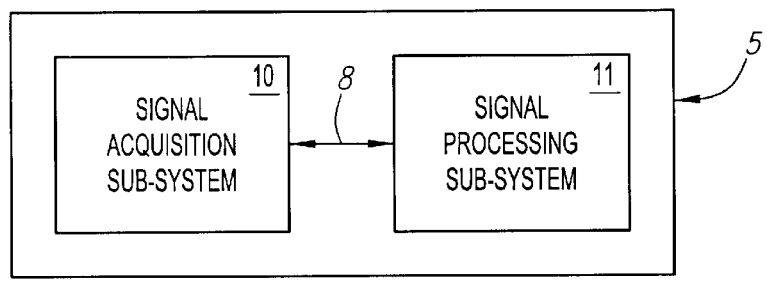
FIG. 1 is a diagram generally depicting a preferred embodiment of a system for measuring pain in a subject, the system being generally referred to herein as an objective pain measurement (OPM) system.

A preferred embodiment of a system and method for measuring pain in a subject is practiced using an objective pain measurement (OPM) system 5 illustrated, by way of example, in FIG. 1. Preferably, the OPM system 5 includes a signal acquisition subsystem 10, a signal processing subsystem 11, and a communication link 8 between the two subsystems 10, 11. The OPM system 5 may be implemented by separating the functional elements for signal acquisition and signal processing if remote analysis of locally acquired pain signal data is desired. However, the OPM system 5 is preferably implemented in one location. Thus, the communication link 8 between the signal acquisition subsystem 10 and the signal processing subsystem 11 may be internal to the processing architecture of the OPM system 5. For example, the communication link 8 may be an electrical connection between two hardware components that respectively perform the functions of the two subsystems 10, 11. Generally, information is communicated over the communication link 8 from the signal acquisition subsystem 10 to the signal processing system 11. However, the communication link 8 may also be bi-directional (as shown in FIG. 1) for certain applications, such as in a network-based system, as described hereinafter. Alternatively, the subsystems 10, 11 may be implemented in software such that the link 8 is software implemented. In another alternate embodiment, the two subsystems 10, 11 lack a communication link 8, using instead, for example, shared memory. If the subsystems 10, 11 are in different locations, the communication link 8 may be any convenient means for remote communication, including various forms of wired and wireless communications.

Figure 2:
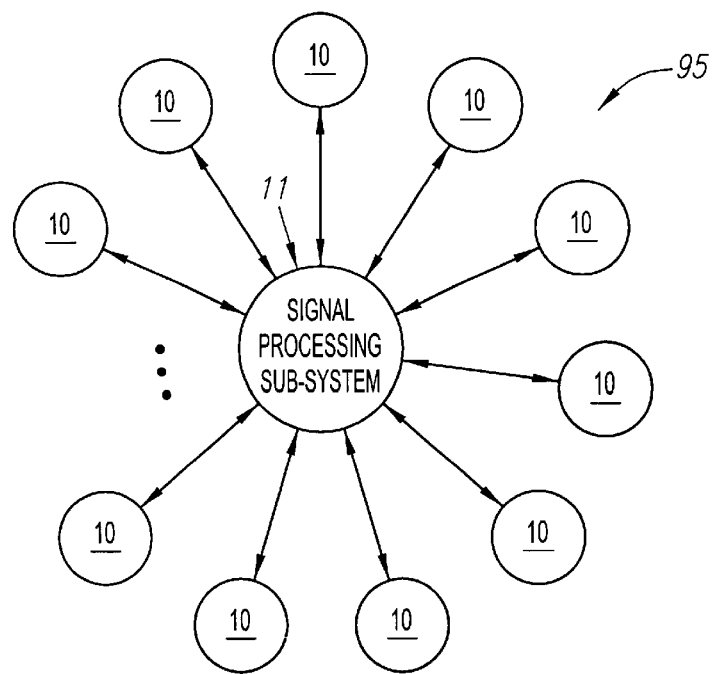
FIG. 2 is a diagram illustrating, by way of example, a preferred embodiment of an objective pain measurement system implemented as a network wherein a centralized signal processing subsystem is networked to a plurality of signal acquisition subsystems 10 as generally depicted in FIG. 1.

FIG. 2 illustrates an example of a preferred embodiment of an OPM system implemented as an OPM network 95 where a centralized signal processing subsystem 11 is networked to a plurality of signal acquisition subsystems 10. FIG. 2 depicts ten signal acquisition subsystems 10 with a single signal processing subsystem 11 as an example of one possible network configuration 95 of the OPM system 5. It is understood that the OPM network 95 is not inherently limited in terms of the number of connected subsystems 10, 11. Specifically, in the embodiment shown in FIG. 2, OPM data is collected at one location and evaluated at another location. The data may be provided from one of the signal acquisition subsystems 10 to the signal processing subsystem 11 by any available means of communication. In one embodiment, the communications for the OPM network 95 are implemented using Internet Communication or switched telephone line services, such as using 56 Kbps modems or ISDN interfaces. The OPM network 95 is also optionally adapted to high-speed access over available high-speed links, such as T1, T3, ADSL, telephone lines, cable modems or other means of high-speed access. The communications are alternatively implemented using available wireless communicating means, including, for example, satellite systems, terrestrial systems, or Blue Tooth. In an Internet communication configuration, preferably the signal acquisition subsystems 10 securely communicate with the signal processing subsystem 11 via an Internet website that preferably requires log-in and password entry. In a preferred embodiment, a mechanism is provided for Internet transmission of collected data from the signal acquisition subsystems 10. Furthermore, the transmission mechanism may allow users associated with the signal acquisition subsystems 10 to retrieve analyzed data, preferably in the form of pain measurement reports. The retrieval process preferably allows the users to have the reports securely downloaded, e-mailed, faxed or otherwise sent to the signal acquisition subsystem 10, to a fax machine, or to any other data output computer or terminal that can display, produce, or otherwise output analysis reports. The retrieval process further allows the reports to be sent by traditional mail. Optionally, an invoice for the service of generating the reports may be transmitted or otherwise sent to the user along with the report.

The signal acquisition subsystem 10 may also be a portable device that collects pain signal data and stores the data for further signal processing at a later time. In one preferred embodiment, the signal acquisition subsystem 10 is conveniently carried by the subject during normal activity over a prescribed period (e.g., 24 hours). During this period, the signal acquisition subsystem 10 collects and stores raw pain measurement data. Then, at a convenient time, the data from the signal acquisition subsystem 10 is downloaded or otherwise transmitted to a signal processing subsystem 11 for analysis. The portable signal acquisition subsystem 10 may be similar to the Holter-type device used for cardiac applications. The download procedure may take place, for example, in a doctor's office or hospital that the patient visits after the data acquisition period. Alternatively, the download procedure may occur remotely, such as via a distributed electronic network (e.g., Internet). A physician or other care provider may then process the raw pain signal data from the signal acquisition subsystem and obtain the patient's pain profile for the signal collection period. Accordingly, the doctor or other care provider can then consider the pain profile results with other observations in order to make a diagnosis and recommend patient treatment.

In another embodiment, the OPM network 95 is wholly implemented in a local area (such as within a clinic or hospital), as a local network (such as an Intranet, client-server system, or other similarly sized network). In this aspect, the communications are preferably implemented using local network systems and protocols such as Ethernet, TCP/IP, parallel port, serial port, and the like. A wireless data communication system is optionally implemented, preferably using infrared, RF, or one of the ISM (Industrial, Scientific and Medical) bands, or other frequencies.

Figure 3:
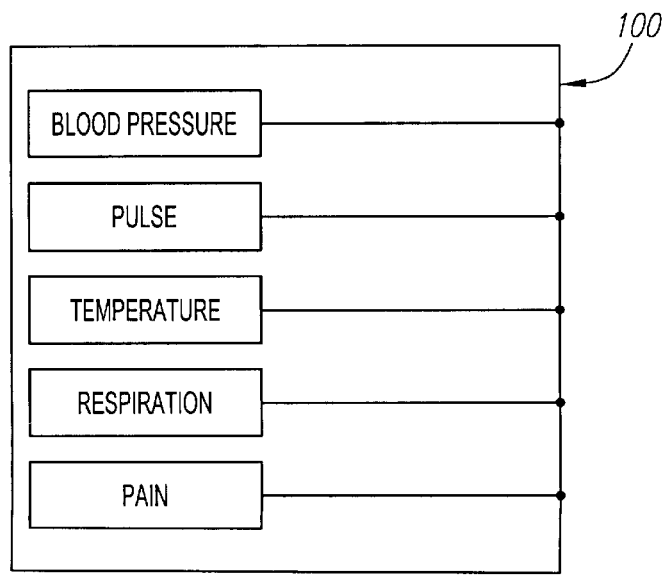
FIG. 3 illustrates, by way of example, a physiological signal measuring device for objectively measuring blood pressure, pulse, temperature, respiration and pain level.

In yet another embodiment, the OPM system 5 is a fully-integrated, compact device in which many of the functional elements may be rendered on an integrated circuit, such as an ASIC. In one such embodiment, the OPM system 5 may be conveniently integrated with other physiological signal measurement devices, for use, for example, in a doctor's office or in a hospital (e.g., emergency or operating room). An integrated device for measuring multiple physiological signals is conceptually illustrated in FIG. 3. FIG. 3 illustrates, by way of example, a physiological monitoring system 100, including components for measuring blood pressure, pulse, temperature, respiration and pain level. Alternatively, a physiological monitoring system may include a component for objectively measuring pain level along with other monitoring components. In a preferred embodiment, each of the measurements is taken using an objective measurement instrument.

In another form of an OPM system 5, the OPM system 5 is implemented as a fully integrated compact device, including a reusable sensor apparatus embedded within the device. The OPM system 5 may be in a form of a color-coded strip. The OPM strip preferably acquires and processes the pain signal using analog circuitry, and preferably presents the pain result as a specific color scale or gray scale intensity. The OPM strip may generally implement the OPM system 5 in a simplified form. In addition to (or in place of) the color or gray scale, the OPM strip may provide a discrete pain reading (similar to forehead thermometers), using, for example, a four category color-coded display (No Pain, Mild Pain, Moderate Pain, and Severe Pain).

The OPM strip preferably includes conductive sensors, analog amplification and filtering circuitry, analog processing circuitry, and a color display. The analog processing circuitry integrates the pain signal in the relevant frequency bands. Optionally, the OPM strip may presume negligible motion artifacts.

To use the strip, the subject is preferably positioned (e.g., reclining) so as to remain stationary. This may help reduce signal artifacts caused by movement and may increase the accuracy of the pain reading. The OPM strip is then firmly attached to the forehead of the subject. A period of time is permitted to elapse while the subject remains stationary. After the prescribed period has elapsed, the strip may then be removed from the forehead of the subject and examined to determine the severity of the subject's pain.

Figure 4:
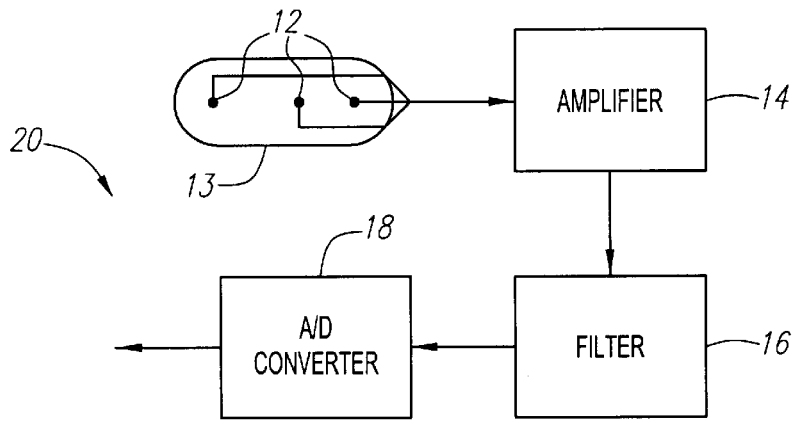
FIG. 4 is a diagram detailing a preferred embodiment of a signal acquisition subsystem, such as is depicted generally in FIG. 1.

FIG. 4 details preferred elements of the signal acquisition subsystem 10, 20 in the OPM system 5. The signal acquisition subsystem 10, 20 preferably includes a set of electrodes 12 on a sensor array 13, which optionally may be in the form of a sensor strip, (various embodiments of which are described herein). The signal acquisition subsystem 10, 20 preferably further includes an amplifier 14, a band-pass filter 16 and an analog-to-digital (A/D) converter 18. Optionally, the signal acquisition subsystem 10, 20 further includes a component for electrically isolating the subject, such as an optical isolator, and a memory (not shown) or other recording means for storing digitized data for further processing. In an alternative embodiment, the signal acquisition subsystem 10, 20 lacks an analog-to-digital converter. In this embodiment, the acquired signal information may be stored on an analog recording device, such as magnetic tape. The signal acquisition subsystem 10, 20 may also include a power source (not shown) that supplies the power to operate any array circuitry associated with or part of the sensor array.

Figure 5:
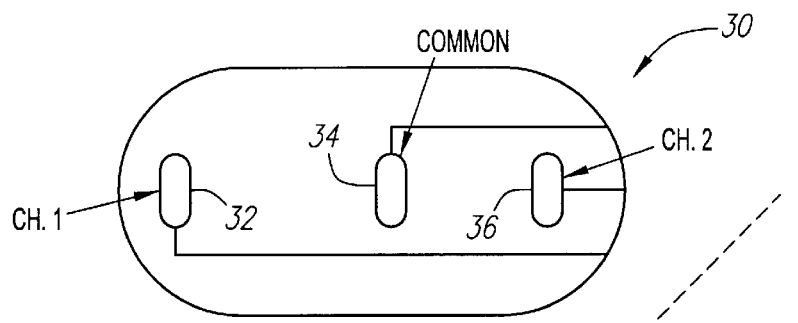
FIG. 5 is a diagram illustrating one example of a sensor array, in the form of a sensor strip, for application, preferably, on the forehead of a subject.

One example of a sensor array is depicted in FIG. 5 in the form of a sensor strip 30. The electrodes 32, 34, 36 preferably are surface electrodes that contact the subject's skin surface. More preferably, the electrodes 32, 34, 36 each have a single contact and in combination comprise a left channel electrode 32, a right channel electrode 36 and a reference electrode 34. Preferably, the array, is applied to the subject's forehead such that left channel electrode 32 is positioned on the left side of the subject's forehead, and right channel electrode 36 is positioned on the right side of the subject's forehead so that it substantially mirrors the location of left channel electrode 32. Reference electrode 34 is preferably positioned midway between the left channel electrode 32 and right channel electrode 36, generally in the middle of the subject's forehead. See FIG. 6. Preferably, signal detection and measurement is performed at each electrode 32, 34, 36.

In general, electric potential changes (electrical activity) on the subject's skin surface are generated by several sources, including background electroencephalographic (EEG) activity, electrodermal activity, electromyographic (EMG) activity, motion artifacts (such as caused by eyeball, eyelid and head movements), and other electrophysiological phenomena. Referring to FIG. 5, the sensor array 30 comprising the left and right channel electrodes 32, 36, enables the OPM system 5 to perform pain detection and pain quantification based on the signals detected from the electrodes 32, 34, 36. Pain detection uses both the left and right channel electrodes 32, 36 to distinguish pain signals from other signals in the relevant frequency range. Electrodes 32, 36 are preferably placed on the subject's forehead, with the left and right channel electrodes 32, 36 symmetrical about the subject's vertical midline. See FIG. 6. In general, background EEG measurements from each side of the vertical midline are negatively-correlated. Other artifacts, such as those caused by eyeball movement, are likewise negatively correlated. In contrast, pain signals from each side of the vertical midline are generally positively correlated and may override the negatively correlated EEG activity. Consequently, pain detection preferably uses positive correlation as a discriminant for pain signals when the measurements are taken from electrodes located on opposite sides of the subject's vertical midline.

The pain detection may also use signal linearity to distinguish pain. This is because pain signals detected from each side of the vertical midline are generally linearly related. In contrast, various artifacts in the detected signal, even those that are positively correlated (e.g., eyelid or head movements), are often not linearly related; thus, artifacts may be distinguished from pain signals based on this additional discriminant.

In an alternate embodiment, electrodes 32, 36 are not on the subject's forehead but remain substantially symmetrical with respect to the subject's vertical midline. For example, the electrodes 32, 36 may be optionally placed on the subject's scalp, symmetrical about the vertical midline where it extends over the top of the subject's head. In this case, electrodes 32, 36 are still placed on either side of the vertical midline. Hair on the subject's head may be removed to minimize signal interference.

Pain quantification may use a single signal channel. In a preferred embodiment, an electrode used only to measure signals for pain quantification is placed on the subject's head. However, any location on the subject, such as an arm, leg, or torso, may also be used. In an OPM system 5 that performs pain quantification, the sensor array may comprise a single signal electrode and a reference electrode.

Alternatively, two or more signal channels may be used for pain quantification. In one such embodiment, the sensation of pain is separately quantified for signals coming from each side of the vertical midline, and the stronger of the two pain signals is used to measure pain intensity. It is desirable to use signals obtained from each side of the vertical midline because pain originating on one side of the subject (e.g., right hand, left foot, etc.) may have a contralateral representation. That is, the pain may be perceived and/or detected by the OPM system 5 primarily on the side of the vertical midline opposite the pain's source. Beneficially, intensity measurements from multiple channels may also be averaged, combined or otherwise used together to provide a final pain intensity measurement. Multiple channels may also be used to determine where (e.g., left or right side) the subject's pain source is located.

Functionally, the electrodes 32, 34, 36 detect electrical activity changes, i.e., voltage changes, between two contacts of each electrode. Typically, the detected magnitude of electrical activity is in the range of 0 to about 500 microvolts. In the embodiment depicted in FIG. 5, a ground electrode 38 is separately provided from the sensor array 30 (here in the form of a sensor strip) and positioned elsewhere on the subject, such as an arm or leg.

The electrodes 32, 34, 36 are preferably circular, oval or ellipse-shaped and positioned vertically relative to the sensor array 30, when it is located on the subject's forehead. These shapes provide each electrode with significant skin contact area while maintaining a functionally desirable distance between each electrode 32, 34, 36. Alternative electrode shapes and configurations that correspond to equivalents known in the art may also be used.

The voltage levels detected by the electrodes 32, 34, 36 are transmitted to an amplifier 14, preferably located off of the sensor array 30. See FIG. 4. Alternatively, or in addition to external amplification, the sensor array 30 may include amplifier circuitry 14 that amplifies the signals from electrodes 32, 34, 36 into a desired voltage range. In a preferred embodiment, the voltage range is between zero and about five volts.

As another option, the sensor array 30, 13 includes preamplifiers (not shown) proximal to electrodes 32, 34, 36 on the sensor array 30, 13. These preamplifiers perform initial signal amplification without amplifying subsequently acquired noise contributions. As another option, the sensor array 30, 13 includes dedicated active and/or passive filters to remove electrophysiological artifacts, radio frequencies and other electromagnetic interference.

In yet another embodiment, the sensor array 30, 13 includes fiber optic connections from electrodes 32, 34, 36 to amplifier 14. In this embodiment, the sensor array 30, 13 includes transducers (not shown) that convert electrical signals from electrodes 32, 34, 36 to light signals. The light signals are then propagated through optical fibers and reconverted to electrical signals by a converter at the amplifier 14. If the sensor array 30, 13 includes preamplifiers, the optical fibers may also communicate the signal between the preamplifiers and the amplifier 14.

The use of optical fiber to communicate the signal to the amplifier 14 reduces additional noise typically caused by signal transmission from electrodes 32, 34, 36. Furthermore, the optical fibers may provide the desired optical isolation between the subject and the rest of the signal acquisition subsystem 10, 20.

Once the signals from electrodes 32, 34, 36 are amplified, the signals from the left and right channels preferably pass through a filter 16 to remove contributions outside a frequency range, preferably about 0.1 Hertz to about 5 Hertz. The applicants have found that within this general frequency range electrical signals corresponding to the intensity of the subjective experience of pain may exist for substantially all subjects. Furthermore, signals between about 0.5 Hertz and about 2 Hertz appear to carry the bulk of pain intensity information. As a result, the circuitry on the sensor array 30, 13 may include capacitive, inductive and/or resistive components to perform the band-pass filtering in the desired range, whether from about 0.1 Hertz to about 5 Hertz, from about 0.5 Hertz to about 2 Hertz, or another convenient range within the more general range of about 0.1 Hertz to about 5 Hertz. In this and other embodiments, filtering may take place before the signals are amplified.

In this embodiment, the signals are preferably received at the A/D converter 18, which digitizes the analog signals into discrete digital samples. See e.g., FIG. 4. The sampling of the signal at the A/D converter 18 should be greater than about 10 Hertz. But oversampling may be used to improve accuracy, and so the preferred sampling rate is in a range around about 250 Hertz. In another embodiment, the filter 16 may include a digital filter implemented on a signal processor after the A/D converter 18 has digitized the signal.

Figure 6:
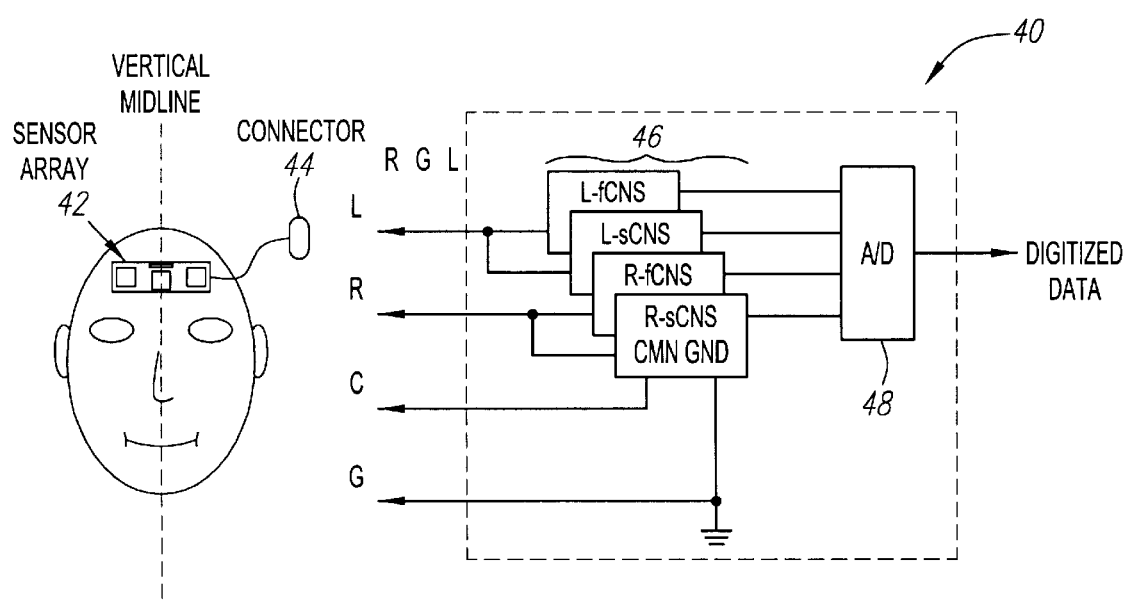
FIG. 6 is a diagram detailing an embodiment of a signal acquisition subsystem, such as is depicted generally in FIG. 1.

FIG. 6 depicts an alternative embodiment of a signal acquisition subsystem 10, 40 that generates digitized sample data for further signal processing. The signal acquisition subsystem 10, 40 preferably performs signal acquisition and signal conditioning before the digital signal is further processed for pain detection and quantification. Signal conditioning preferably uses a multi-channel variable gain and a spectral shaper (not shown). The conditioned signal is preferably obtained with a 16-bit A/D converter, 48, at a sampling frequency of preferably about 250 Hertz.

In the embodiment depicted in FIG. 6, the signal acquisition subsystem 10, 40 acquires electrophysiological signals from a subject's forehead for further processing and integration by the signal processing subsystem 11 (not shown). The signal acquisition subsystem 10, 40 includes multi-channel, signal-specific, differential amplifiers 46. The amplifiers 46 are individually tuned according to signal type, ranging from medium-gain, very-low-frequency amplifiers (60 dB, 0.1–2 Hertz) for acquisition of slow central nervous system (sCNS) signals, to high-gain, medium-frequency amplifiers (80 dB, 2–100 Hertz) for acquisition of faster CNS (fCNS) signals. Preferably, the signals are acquired using a sensor array 42 attached to the subject's forehead and designed for optimal reception of the electrophysiological signals. The sCNS and fCNS signals are then processed separately, quantified, and integrated to provide a sensitive, specific, and accurate reading of pain level.

In another preferred embodiment, the signal acquisition subsystem 10, 40 performs the steps of conditioning fCNS and/or sCNS signals (e.g., by amplification & spectral shaping), and digitizes the signals, most preferably using data sampling and storage.

Figure 7:
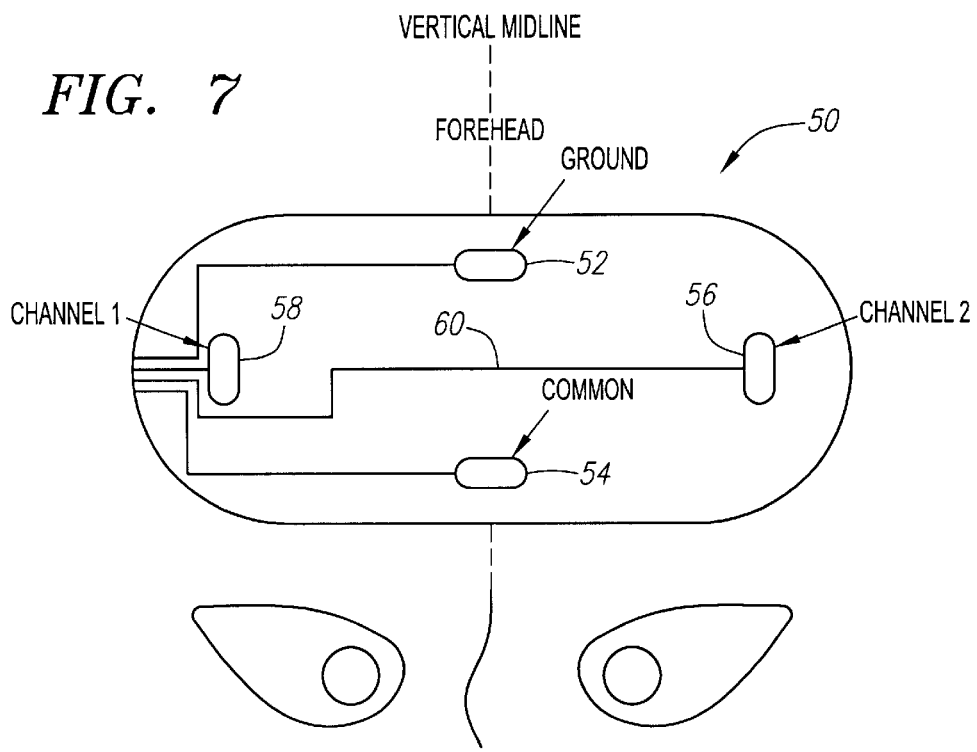
FIG. 7 is a diagram illustrating another example of a sensor array for application, preferably, on the forehead of a subject, such as is generally depicted in the signal acquisition subsystem of FIG. 6.

Importantly, each of the sensor arrays described herein may include one or more of the optional components discussed in connection with sensor array 30, depicted in FIG. 5. Moreover, FIGS. 6, 7, 8 and 9 detail specific preferred embodiments of a sensor array. For example, FIG. 7 depicts a preferred sensor array embodiment 50, 42. The preferred sensor array 50 includes left and right channel electrodes 56, 58, a common electrode 54 and a ground electrode 52 on the sensor array 50 above the array's center point 60. Alternatively, the positions of the ground electrode 52 and the common electrode 54 may be exchanged. Preferably, the ground electrode 52 is substantially shaped as a horizontally-oriented oval or ellipse. Similarly, the common electrode 54 is substantially shaped as a horizontally-oriented oval or ellipse and located below the center point 60 of the sensor array 50. The horizontal orientation of the ground and common electrodes 52, 54 preferably preserves a functional distance between them while providing each with a substantial contact area.

Figure 8:
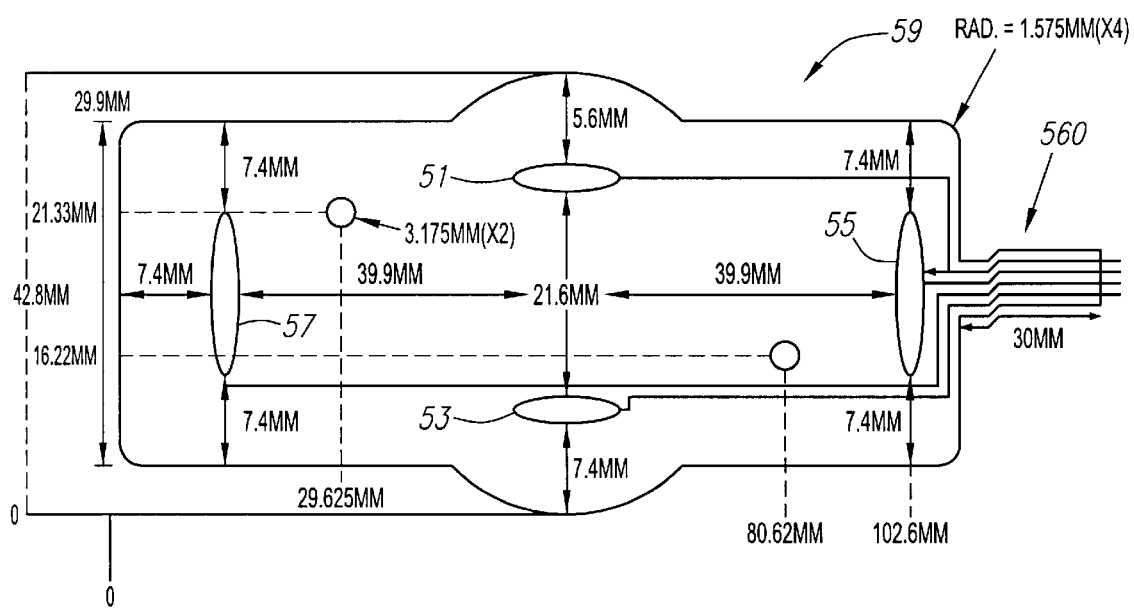
FIG. 8 is a diagram illustrating another example of a sensor array for application, preferably, on the forehead of a subject, such as is generally depicted in the signal acquisition subsystem of FIG. 6.

FIG. 8 depicts a detailed view of a second preferred embodiment of a sensor array 24. This sensor array 59 includes electrodes 51, 53, 55, 57 that correspond in function and general location to electrodes 52, 54, 56, 58 illustrated in FIG. 7. However, sensor array 59 has preferred dimensions, that include the size, shape and location of the electrodes 51, 53, 55, 57. In a most preferred embodiment, the electrodes are substantially elliptical and have a major axis length of about 15 mm and a minor axis length of about 4 mm. The particular size and shape of the sensor array 59 and the size, location, and shape of the electrodes is designed to maximize the signal to noise ratio in the relevant frequency range for a wide variety of patient forehead sizes and shapes. FIG. 8 also discloses a tail 500 for combining the lines from each electrode onto a single cable and terminating the lines at a connector 44. This feature may be used with any sensor array.

Figure 9:
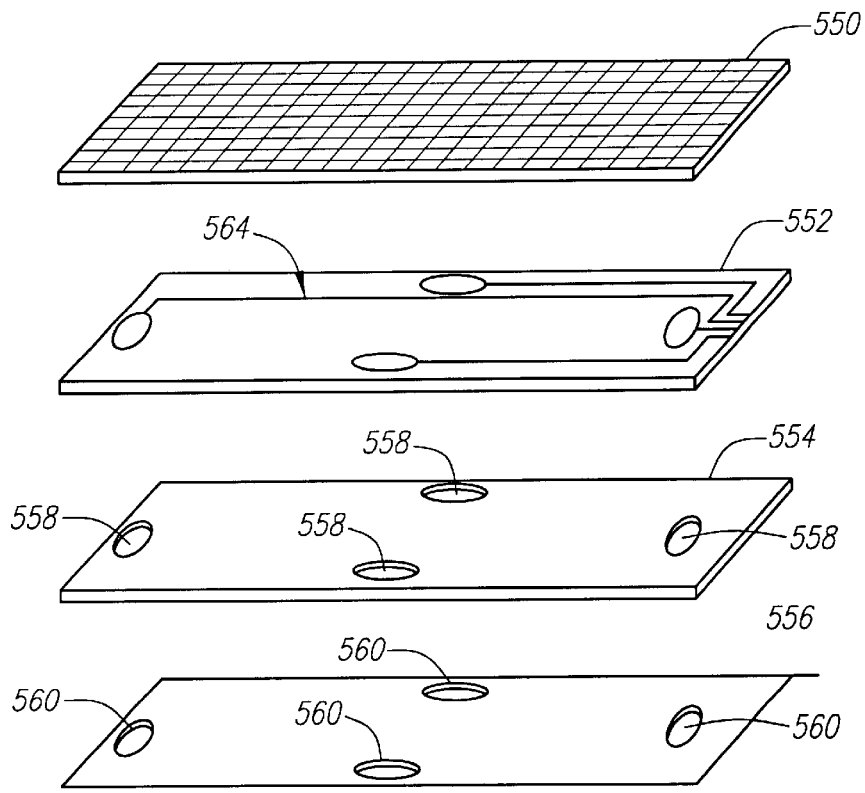
FIG. 9 is a diagram illustrating an exploded view of an example of a sensor array for application, preferably, on the forehead of a subject, such as is generally depicted in the signal acquisition subsystem of FIG. 6.

As shown in FIG. 9, the sensor arrays described herein preferably comprise several layers of bio-compatible material for detecting electrical activity. FIG. 9 illustrates an exploded view of the layers of sensor array 30 of FIG. 5. The layers of the sensor array preferably include an optional top shielding layer 550, a printed circuit layer 552 beneath the optional top shielding layer 550, an articulated foam layer 554 beneath the printed circuit layer 552, and, optionally, an adhesive layer 556 beneath the articulated foam layer 554.

The shielding layer 550 is preferably comprised of a conductive material formed as a grid (e.g., a silver ink grid) and provides shielding from various potentially interfering sources that may reduce the available signal-to-noise ratio. The shielding layer 550 preferably shields the electrodes 51, 53, 55, 57 from potential electrical, radio frequency and other electromagnetic interference, including, in particular, relatively high frequency noise (greater than about 10 Hertz) modulated by relatively low frequency noise (less than about 5 Hertz), which may contaminate the pain signal.

The printed circuit layer 552 preferably comprises an insulating, non-conductive material, such as appropriate polymer-based plastics, as are well known in the art. Preferably, the printed circuit connections for the sensor array are located on the material's underside. The printed circuit connections may comprise a conducting material for carrying the electrical signal, such as silver ink. The circuit connections extend from one edge of the printed circuit layer 552 to the locations of the respective electrodes. At the electrodes' respective locations, the silver ink print (or other conductor print) is appropriately shaped (e.g., oval or elliptical) and forms the electrode contact at the printed circuit layer 552. Preferably, at the location of each electrode, the print is coated with an electrical interface material, such as silver chloride. Because a conducting gel initially carries the electrical signal from the subject's skin to the printed circuit layer 552, the electrical interface material is preferably used between the conducting gel and the circuit print to reduce any buildup of static charge and/or polarization effect occurring at the interface of the two materials.

The articulated foam layer 554 is comprised of any appropriate insulating nonconductive material as is known in the art, and has holes 558 that are preferably substantially shaped like and sized like the electrodes 51, 53, 55, 57 at the electrodes' locations. The foam layer 554 is preferably smooth and flexible so as to easily contour to the subject's skin surface. Preferably, a conductive gel, preferably hydrogel or wet gel, fills the holes 558 and extends to the next layer (e.g., the adhesive layer 556), if one exists.

The optional adhesive layer 556 also includes holes 560 that are preferably shaped like and sized like the electrodes 51, 53, 55, 57 at the electrodes' locations. Like the articulated foam layer 554, the adhesive layer 556 is preferably smooth and flexible so as to easily contour to the subject's skin surface and so the layer remains stationary once affixed on the subject's skin.

Figure 10:
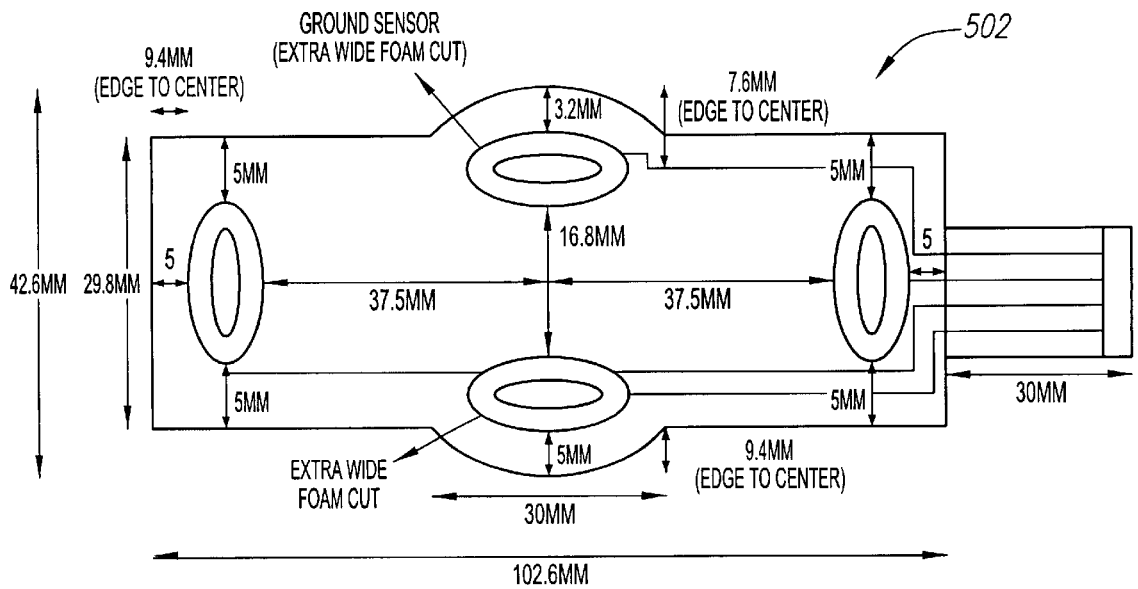
FIG. 10 is a diagram illustrating another example of a sensor array for application preferably on the forehead of a subject, such as is generally depicted in the signal acquisition subsystem of FIG. 6.

FIG. 10 illustrates an alternative configuration of a sensor array 502 that has alternative dimensions, locations and sizes for the electrodes. The sensor array is preferably configured for use with a wet conductive gel.

Referring again to FIG. 1, in a preferred embodiment of the OPM system 5, the output of the data acquisition subsystem 10 is transmitted to a signal processing subsystem 11. Contemporary forms of transmission include Universal Serial Bus, PCMCIA card, PCI card, SCSI, FireWire, and Blue Tooth. FIG. 11 details one specific hardware embodiment of a signal processing subsystem 60, 11, such as that generally depicted in FIG. 1.

In FIG. 11, the signal processing subsystem 60, 11 preferably includes a processor 62 and a memory storage 64. The signal processing subsystem 60, 11 further may include an output interface 66 such as a video display and/or a speaker, and an input interface 68 such as one or more knobs, a touch panel, a keyboard, a mouse and/or a microphone. Via the input interface 68, a user may control the operation of the signal acquisition subsystem 10 by issuing commands, processed by the processor 62, that begin and end digital data receipt and storage. The digital electronic activity signals received by the processor 62 are optionally displayed on the output interface 66 (e.g., video display) and stored in memory storage 64. Preferably, the output interface 66 graphically displays the signal processing results from the processor 62.

The signal processing subsystem 60, 11 may comprise a computer (like those manufactured by IBM® or Apple®) with a monitor, such as a cathode ray tube (CRT) or liquid crystal display (LCD). Computer software may be used for the signal processing subsystem 60, 11 because software provides flexibility in programming and modifying the software, displaying results, and running other peripheral applications. Alternatively, the signal processing subsystem 60, 11 may be implemented using any type of processor or processors that analyze electrical activity measurements as described herein. Thus, as used throughout, the term "processor" refers to a wide variety of computational devices or means including, for example, using multiple processors that perform different processing tasks or having the same tasks distributed between processors. The processor(s) may be general purpose CPUs or special purpose processors, such as those often used in digital signal processing systems. Further, multiple processors may be implemented in a server-client or other network configuration or as a pipeline array of processors. Some or all of the processing may be alternatively implemented with hard-wired circuitry such as an ASIC, FPGA or other logic device. In conjunction with the term "processor," the terms "memory" and "computer media storage" refer to any storage medium that is accessible to a processor that meets the memory storage needs for the OPM system 5 or its components.

FIG. 12 illustrates a preferred embodiment of the functional elements of a signal processing subsystem 60 previously represented in an exemplary configuration hardware in FIG. 11. As depicted in FIG. 12, the signal processing subsystem 60 preferably includes a signal preparer 69, a pain intensity quantifier 61, a pain detector 63, a confidence assessor 65 and an output interface 67. As referenced above in the definition of a "processor," the signal preparer 69, the pain intensity quantifier 61, the pain detector 63, and the confidence assessor 65 may be implemented in separate processors, in a single processor or in any other convenient configuration. The signal preparer 69 preferably normalizes the data to account for signal gain variations and noise. Preferably, the data is then channeled into two processors, (most preferably operating in parallel), comprising the pain detector 63 and the pain intensity quantifier 61. The pain detector 63 determines whether pain exists in the subject. The pain intensity quantifier 61 measures the level of pain in the subject. In one embodiment, the pain intensity quantifier 61 executes a primary algorithm or process for quantifying a pain level from an extracted pain signal. Further, the pain detector 63 preferably executes an auxilliary algorithm or process that uses complementary data to determine whether pain exists and to increase the pain readings' specificity and sensitivity. The output from each processor 61, 63 is input to the confidence assessor 65, which then outputs the result to the output interface 67. The output interface 67 in turn presents the data to the OPM system user.

FIG. 13 illustrates one embodiment of a signal preparation method 70 performed by a signal preparer, such as the signal preparer 69 represented in FIG. 12. Preferably, the input to the process 70 is the global sample set of discrete signal values from a signal acquisition subsystem 10. In one step 72, the mean of the global sample set of discrete sample values is determined. In another step 74, the calculated mean is substracted from each of the sample values in the global sample set. The resulting set of values represents a zero-mean sample set. In another step 76, a band-pass filter is optionally applied to the zero mean sample set. In yet another step 78, the filtered sample set is normalized to account for variations in the acquired signal due to the physical differences between subjects.

In another step 79, the normalized global sample set is divided into segments preferably of a fixed size. Preferably, the particular size of the segments is determined to optimize for pain signal measurement. The preferred segment sizes are based on the pain signal's spectral characteristics, which affect the desired segment time. Most preferably, for a frequency range of about 0.1 Hertz to about 5 Hertz, the segment time should be between about four seconds and about 20 seconds. Thus, for example, using a preferred sampling rate of 250 Hertz, the preferred size of each segment is in the range of about 4000 samples per segment.

The signal preparation method 70 may be mathematically expressed as follows:

$$x = x(i) = y(i \cdot \Delta T) \qquad (1)$$

Here, y is the continuous analog measurement, $\Delta T$ is the sampling period, and i is the sample number. The zero-mean sample set may then be expressed as follows:

$$\tilde{x}(i) = x(i) - \bar{x}, \qquad (2)$$

where $\bar{x}$ is the mean of x and $\tilde{x}(i)$ has a zero mean. In another step, a band pass filter is optionally applied:

$$x_{BPF}(i) = \sum_{j=1}^{Q} b_j \cdot \tilde{x}(i-j) \qquad (3)$$

where $$\sum_{j=1}^{Q} b_j = 1,$$

j is an index into the window of width Q of the band pass filter, $b_j$ are band pass filter coefficients, and $X_{BPF}(i)$ are filtered values of the signal.

In another step, the signal values are preferably normalized to account for differences in signal acquisition between subjects who have been given the same pain stimulus. Differences in the acquired signal may be caused by variations in the characteristics and/or quality of the signal propagating media of the subjects such as, for example, differences in bone thickness, skin conductance/impedence, and other electrophysiological properties. These differences may be caused by the subject's age, gender, dehydration, mood, and the like. Preferably, the signal values are normalized so as to cancel out the effects of these differences.

The signal values may be normalized in any number of ways. In one embodiment, the signal values are divided by a normalizing term such as the variance (or standard deviation) of the signal values. Thus, mathematically, the normalization may be expressed as:

$$x_N(i) = \frac{x_{BPF}(i)}{\sigma_x} \qquad (4)$$

where $\sigma_x$ is the standard deviation of $x_{BPF}(i)$, and $x_N(i)$ are normalized values for x(i). Alternatively, a variance (or standard deviation) term may be determined based on samples taken outside of the relevant pain frequency range to avoid any contribution by the pain signal itself to the normalizing term. In other embodiments, the normalization step may be based on an assessment of one or more physical characteristics of the subject that relate to the variations in the acquired signal.

Preferably, in another step, the global sample is divided into M segments, each having L samples, where k is a sample index in each segment, U is the number of samples between segments and p is the segment number. Thus, $$x_{N,p}(p \cdot U + \kappa) = x_N(i) \qquad (5)$$

where $1 < k < L$, $0 < p < M$. As may be seen from Equation (5), where U<L, the M segments in the global sample set may partially overlap each other.

In another embodiment, the acquired signal from the signal acquisition subsystem 10 is preprocessed for rejection of motion and other artifacts and then normalized to reduce inter- and intra-subject signal variability. In this embodiment, the signal preparation (preprocessing) steps generally include: a segmentation step, preferably by grouping a predetermined number of samples to form a data segment; a mean subtraction step, preferably by subtracting the mean value sample by sample from each data segment; and a normalization step of each data segment, preferably by signal variance. Optionally, the segmentation step may be performed after the mean substraction step and the normalization step. In this case, the mean and variance values are based on the global data set.

Signal conditioning, acquisition and preparation (preprocessing) may be accomplished, for example, by using the following mathematical steps:

Digitization: In this step, amplitude measurements (e.g., in microvolts) are preferably taken from either of the preferably two available channels (left or right electrode) and digitized. This step may be represented by the equation (Eqn. 6):

$$x^1(n) = x^0(n \cdot \Delta T), \quad (6)$$

such that $\Delta T = 1/F_s$ where $\Delta T$ is the sampling period (e.g., 4 msec) and $F_s$ is the sampling frequency (e.g., 250 Hertz). In the above equation, n is the sample number, $x^0$ are the measured analog values, and $x^1$ are the discrete sample values.

Segmentation: In this step, the signal values are parsed into segments of L samples, where a new segment begins with the first sample following the last sample in the previous segment. Thus, sets of segments preferably are defined by:

$$x_{k,L}^1(n) = x^1(k \cdot L + n), \quad (7)$$

where 1000<L<5000, k=1,2, . . . , K, there are K segments and k is the segment number.

Mean subtraction: In this step, the mean within a segment is subtracted from the value of each sample in the segment. This step is preferably performed for all segments in the data set. Thus, this step may be expressed as:

$$x_k^3(n) = x_k^2(n) - AVG\{x_k^2(n)\} \quad (8)$$

Normalization: In this step, the signal values are normalized. In one embodiment, the normalization step is performed by dividing each sample by the variance of the sample set, preferably the global sample set, but optionally the sample set for each segment. Thus, this step may be represented by:

$$x_k^4(n) = \frac{x_k^3(n)}{VAR\{x_k^3(n)\}} \quad (9)$$

A preferred embodiment of a method of performing pain detection, such as performed by the pain detector represented in FIG. 12, makes use of two processed signals. Preferably, the normalized and segmented data sample set serves as an input to the pain detection process (such as that output from FIG. 7B's signal preparer 69. As discussed above, the pain detection method determines whether the signals from the left and right channels are positively correlated and whether the signals from the two channels are linearly related in the relevant frequency band. In one preferred embodiment, the correlation coefficient, ρ, is used to determine whether the signals are positively correlated. The correlation coefficient, ρ, is preferably determined by determining the covariance of the signals from the two channels, according to the following:

$$\rho = \frac{COV[x_i(n), y_i(n)]}{\sqrt{VAR[x_i(n)] \cdot VAR[y_i(n)]}} \quad (10)$$

where $y_i(n)$ are the normalized signal values in a segment from the right channel, $x_i(n)$ are the normalized signal values in the segment from the left channel, $VAR[x_i(n)]$ and $VAR[y_i(n)]$ are the variances for the respective sets of signal values, and $COV[x_i(n), y_i(n)]$ is the covariance between the two channels, meaning that:

$$COV[x_i(n), y_i(n)] = E\{(x_i(n) - \eta_x)(y_i(n) - \eta_y)\} \quad (11)$$

where $\eta_x$ and $\eta_y$ are the means of $x_i(n)$ and $y_i(n)$ respectively. Generally, the correlation coefficient, ρ, has values between −1 and 1.

Similarly, in a preferred embodiment, a coherence, $C_{xy}(\omega)$, of a segment from the left and right channels is evaluated to determine whether the signals are linearly related. This embodiment may determine linearity using the following equation:

$$C_{xy}(\omega) = \frac{|P_{xy}(\omega)|^2}{P_{xx}(\omega) P_{yy}(\omega)} \quad (12)$$

where ω is the frequency in radians based on a sampling frequency F of preferably about 250 Hertz, $P_{xy}(\omega)$ is the cross power spectrum between the two channels, $P_{xx}(\omega)$ and $P_{yy}(\omega)$ are the power spectra for the respective channels, preferably measured between about 0.1 and about 5 Hertz, and $0 \leq C_{xy}(\omega) \leq 1$. Generally, $C_{xy}(\omega)$ increases as a subjective perception of pain increases. Conversely, for low values of $C_{xy}(\omega)$, no pain is generally experienced.

In an alternative embodiment, the pain detection method may include one or more of the following steps:

(a) Band-pass filtering of left and right composite fCNS-sCNS data in a range of 0.1–30 Hertz, and preferably of sCNS data in a range of 0.1–5 Hertz.

(b) Selection of consecutive data segments of left and right channels.

(c) Correlation analysis of the bilateral data segments.

(d) Derivation of confidence coefficient(s) from the correlation analysis.

(e) Return to step (b) until end of recorded data.

In this alternative embodiment, the detection method preferably uses correlation analysis of multichannel fCNS and/or sCNS signals to increase sensitivity (i.e., produce lower false negative rates) and specificity (i.e., produce lower false positive rates) in the pain level readings. Normally, the bilateral fCNS recordings that reflect cerebral activity are negatively correlated, since the recordings are referenced to a center-located common lead. However, during pain periods, sCNS activity may generate correlated surface activity that overrides the anticorrelated cerebral activity. The transition from negative to positive correlation may be detected before onset of a substantial pain signal, and thus its detection increases the sensitivity performance of the detection algorithm in the OPM system 5. Moreover, certain artifacts usually do not cause correlated bilateral activity, and thus the OPM system's specificity performance may be enhanced by rejecting those artifacts using the correlation analysis. Thus, in one embodiment, if the signal is positively correlated, it is classified as containing a pain signal that may be evaluated to determine its magnitude. The pain signal's magnitude may be evaluated using the following calculations. As discussed previously (see Equation (10)), where $x_i(n)$, $y_i(n)$ are concurrent bilateral data segments, the correlation coefficient, $\rho$, for the two signals is defined as:

$$\rho = \frac{COV[x_i(n), y_i(n)]}{\sqrt{VAR[x_i(n)] \cdot VAR[y_i(n)]}} \tag{13}$$

where $|\rho| \leq 1$.

The correlation coefficient, $\rho$, is preferably used for confidence analysis of the corresponding pain level reading. A confidence coefficient, $\eta_{cor}$, is preferably defined as follows:

$$\eta_{cor} = \frac{1}{2} \cdot \left[ sign(\rho) \cdot \sqrt{|\rho|} + 1 \right] \tag{14}$$

to obtain a range of coefficient values between 0 and 1. Alternatively, to obtain a range of values for $\eta_{cor}$ between 0 and 10, a multiplier of 5 (instead of ½), is used. The square-root operator is used so as to enhance the separation of values from the zero-midpoint for the correlation coefficient, or from the 0.5 or 5 midpoint for the confidence coefficient, depending on the multiplier that is used.

The confidence coefficient, $\eta_{cor}$, contributes to the system in at least two ways. First, it provides increased sensitivity because the shift from negative to positive correlation is evident, even with small magnitude pain signals, and thus it can help detect low pain levels. Second, the confidence coefficient helps validate the pain reading, thereby enabling discrimination between true pain signals and artifacts that generally do not elicit the negative-to-positive shift of correlation.

The confidence coefficient may be defined so that it varies from 0 (perfect negative correlation) to 10 (perfect positive correlation), thereby making it easier to visually display (and read) a confidence coefficient diagram, optionally displayed with the primary pain reading.

In an embodiment of a pain detection method where channel correlation and channel coherence are evaluated (e.g., the first detection embodiment described above), two confidence coefficients, i.e., the confidence coefficient, $\eta_{cor}$, from the correlation coefficient, $\rho$, and a confidence coefficient $\eta_{coh}$, based on the coherence determination, may be evaluated and factored into the final pain result. Similar to Equation (14), $\eta_{coh}$ may be expressed as:

$$\eta_{coh} = \frac{1}{2}[sign(2C_{xy}(\omega)-1) \cdot \sqrt{|2C_{xy(\omega)}-1|}+1]$$

where $\eta_{coh}$ has a range of values between 0 and 1. As with the correlation confidence coefficient, $\eta_{cor}$, in Equation (14), $\eta_{coh}$, may be rescaled to values between 0 and 10. The confidence coefficient, $\eta_{coh}$ may also be applied in a similar way to modify the pain result.

FIG. 14 illustrates one embodiment of a pain intensity quantification method 80, such as may be performed by the pain intensity quantifier represented in FIG. 12. In one step 82, the normalized and segmented sample set is transformed into the frequency domain for each segment.

For example, for each segment, the discrete signal is transformed into the frequency domain to obtain the power spectrum for each segment. This may be done using any of a number of methods including directly taking the discrete Fourier transform (DFT) or using linear prediction coding (LPC). LPC is preferably used to perform the transformation for short, non-stationary data segments, such as are normally obtained from the preprocessed pain signal. The following LPC equation is preferably used:

$$x(i) = \sum_{l=1}^{s} a_l \cdot x(i-l) + e(i) \tag{15}$$

where S is the model order and has an integer value preferably in the range of 3 to 10 (e.g., 5), l is an index for the linear description, $a_l$ represents the linear prediction coefficients, and e(i) is the error term in the prediction. In a next step 84, a raw pain signal, R, between frequencies of interest are evaluated for each segment. In another step 86, the raw pain signal is scaled.

In one specific embodiment, the quantified pain signal preferably is extracted to provide a pain level reading using one or more of the following steps:

(a) Band-pass filtering of sCNS data in a range of 0.1–2.0 Hertz;
(b) Selection of consecutive data segment;
(c) Linear prediction of the band-passed signal segment using least-square fitting;
(d) Transformation of the linear prediction parameters into frequency domain;
(e) Non-linear weighted averaging of frequency domain signal;
(f) Taking the logarithm of the weighted average value;
(g) Scaling of logarithm result by calibration coefficients, yielding pain level reading;
(h) Return to (b) until end of recording.

In the above sequence of steps, steps (b) through (e) generally measure the power spectrum for the signal in the relevant frequency range. Steps (f) and (g) generally calibrate and scale the result to obtain a final pain reading. The above sequence of steps may be implemented as follows:

Band-pass filtering (BPF) (a) (0.1–2.0 Hertz): In this optional step, the signal values are preferably filtered so that only effects within the range of about 0.1 to about 2.0 Hertz are determined. This step is represented by the following equation:

$$x_k^5(n) = \sum_{i=1}^{Q} b_i \cdot x_k^4(n-i), \tag{16}$$

In Equation (16) above, $b_i$ are the BPF coefficients, where i is an index into the BPF window and Q is its size.

Power spectrum measurement (b)–(e): In this set of steps, the strength of the signal is evaluated. In one embodiment, the strength may be determined by calculating the signal's power spectrum in the frequency range of interest. To do this, the signal preferably is represented in the frequency domain, which may be achieved using linear prediction analysis. Thus, continuing from equation (16), $x(n) \equiv x_k^5(n)$ is first defined. Generally, the linear prediction formula for $x(n)$ is as follows:

$$x(n) = \sum_{i=1}^{P} a_i \cdot x(n-i) + e(n) \tag{17}$$

where $a_i$ are the linear prediction coefficients, e(n) is the error term in the prediction, n=P+1, ..., N, and P is the model order. Transforming the linear prediction formula to matrix notation:

$$[x(n)]_{(N-P)x1} = [x(n-i)]_{(N-P)xP} \cdot [a_i]_{Px1} + [e(n)]_{(N-P)x1} \quad (18)$$

where $$x(n-i) = \begin{bmatrix} x(P) & x(P-1) & \cdots & x(1) \\ x(P+1) & x(P) & \cdots & x(2) \\ x(P+2) & x(P+1) & \cdots & x(3) \\ \vdots & & & \\ x(N-1) & x(N-2) & \cdots & x(N-P) \end{bmatrix} \equiv \underline{\underline{X}}$$

and $$x(n) = \begin{bmatrix} x(P+1) \\ x(P+2) \\ \vdots \\ x(N) \end{bmatrix} \equiv \underline{x} \quad a_i = \begin{bmatrix} a_1 \\ a_2 \\ \vdots \\ a_p \end{bmatrix} \equiv \underline{a} \quad e(n) = \begin{bmatrix} e(P+1) \\ e(P+2) \\ \vdots \\ e(N) \end{bmatrix}$$

The matrix notation of the linear prediction formula is:

$$\underline{x} = \underline{\underline{X}} \cdot \underline{a} + \underline{e} \quad (19)$$

and the least-square solution of the linear prediction formula is:

$$\hat{\underline{a}} = -(\underline{\underline{X}}^T \cdot \underline{\underline{X}})^{-1} \cdot \underline{\underline{X}}^T \cdot \underline{x} \quad (20)$$

where $\hat{\underline{a}}$ is the estimate for the linear prediction coefficients. The linear prediction coefficients are then transformed to frequency domain to obtain the power spectrum signal:

$$P_{xx}(w) = \frac{\sigma_e^2}{\left|1 + \sum_{k=1}^{P} a_k \cdot e^{-jwk}\right|^2} \sim \frac{1}{\left|1 + \sum_{k=1}^{P} a_k \cdot e^{-jwk}\right|^2} \quad (21)$$

where w is the frequency in radians, $P_{xx}(w)$ is the power spectrum for a segment, and $\sigma_e^2$ is the variance in the prediction error. Preferably, as one measure of the signal strength, the frequency domain squared signal is integrated over the frequency range of interest:

$$R = \sum_{w=w_1}^{w_2} P_{xx}^2(w), \quad (22)$$

where R is the raw pain reading and $w_1$, $w_2$ are frequency summation limits.

Scaling (f)–(g): Having a representation of signal strength, R, additional steps preferably are performed to calibrate and scale R to yield the pain level result for each segment. In one preferred embodiment, the calibration and scaling of R is according to the equation:

$$PAIN = C_1 \cdot \log(R + C_2); \quad (23)$$

where PAIN is the scaled and calibrated pain level, and $C_1$, $C_2$ are calibration coefficients. Given an empirically determined range of values for R, $C_1$ and $C_2$ are chosen so that PAIN ranges from 0 to 10.

Preferably, a setting of $C_2 = 1$ is selected so as to ensure that the numerical value for PAIN is guaranteed to be positive. The log term compresses the range of values onto a logarithmic scale, generally representing the relationship between the raw pain signal and the subjective experience of pain. Other biological sensors, such as the ear and the eye, similarly operate on a logarithmic basis. Furthermore, a setting of $C_1 = 10.0$ is preferably a value determined according to empirical studies to define the value of PAIN=1 as the threshold between a subjective experience of pain and a subjective absence of pain for a predetermined percentage of normal subjects in a baseline test. (Examples of such empirical studies are discussed more fully hereinafter.) These empirical studies demonstrate that a setting of $C_1 = 10$ preferably establishes a threshold of 1.0 between pain and no-pain such that at least about 99% of subjects experience a PAIN value $\leq 1.0$ in the absence of a painful stimulus. Alternatively, $C_1$ may be set to another value to establish a threshold of PAIN=1.0 such that some other percentage of subjects experience a value of PAIN$\leq 1.0$ in the absence of a painful stimulus.

In other embodiments, $C_1$ may be a non-scalar term, such as a linear, quadratic, other polynomial or another function type to scale the raw pain signal according to other convenient or desireable criteria. For example, $C_1$ may be a quadratic or other function so as to produce a pain result that is calibrated to be in general accordance with the conventional VAS scale. As another example, $C_1$ and/or Equation (23) in general may be defined to obtain a particular balance between specificity (i.e., the extent to which affirmative readings of pain by the OPM system 5 are correct) versus sensitivity (i.e., the extent to which the OPM system 5 detects actual experiences of pain). In general, the OPM system has a range of performances that vary in terms of specificity and sensitivity. The $C_1$ term may be set to a particular performance within the range based on predetermined relative priorities of specificity versus sensitivity.

Optionally, the final pain reading, PAIN, is modified by the results of the generation of the confidence coefficients, $\eta_{cor}$ and $\eta_{coh}$. In other embodiments, the confidence coefficients may be used to generate a separate value such as a number between 0 and 100, that represents a percentage of confidence in the quantified pain result. Generation and application of confidence values, such as $\eta_{cor}$ and $\eta_{coh}$, are preferably performed in a processor, such as the confidence assessor 65 depicted in FIG. 12.

One example of an approach to integrating the PAIN value, $\eta_{cor}$, and $\eta_{coh}$, where $\eta_{cor}$ and $\eta_{coh}$ have been scaled to values between 0 and 10, may be expressed logically as follows:

If $(PAIN < 1)$ then $PAIN = PAIN$.

else

If $(\eta_{cor} < 3)$ AND $(\eta_{coh} < 3)$, then $(PAIN = 0)$.

else If $(\eta_{cor} + \eta_{coh}) < 10$, then $(PAIN = PAIN / (11 - (\eta_{cor} + \eta_{coh})))$.

The above logic incorporates several considerations. First, where the quantified PAIN value is very low (e.g., PAIN<1), then the confidence coefficients do not affect the determination. The subject is considered to have no experience of pain. Next, where the PAIN value indicates something other than no pain (e.g., PAIN$\geq 1$), then where both confidence coefficients have low values, the quantified pain signal is considered to represent sources other than an actual experience of pain, and therefore PAIN is set to zero. Where both confidence coefficients are not considered too low to establish that no pain is present, then the PAIN reading is reduced based on the levels of the confidence coefficients. Generally, the lower the values for the confidence coefficients, the more the quantified PAIN result is reduced. Finally, where both coefficients have relatively high values, the PAIN result (which should indicate that pain is present in the subject) is not modified.

In the above example, the two confidence coefficients are given the same weighted effect on the PAIN value. In other embodiments, the confidence coefficients may affect the final PAIN result differently. Furthermore, it can be seen that the confidence coefficients may be applied in a variety of other ways to produce the output PAIN result within a calibrated range.

An OPM system 5 has been extensively tested in several distinct studies. In a first study, an OPM system 5 was tested using a controlled Quantitative Sensory Testing (QST) protocol that employed a Medoc TSA2001 QST device (Medoc Ltd., Ramat Yishai, Israel). The protocol included application of a gradually increased heat stimulus to a subject's palm. The temperature stimuli ranged from 32 to 48° C. The subject was instructed to report a subjective pain level using Medoc's Computerized VAS (CoVAS) throughout the experimental session.

Figure 15:
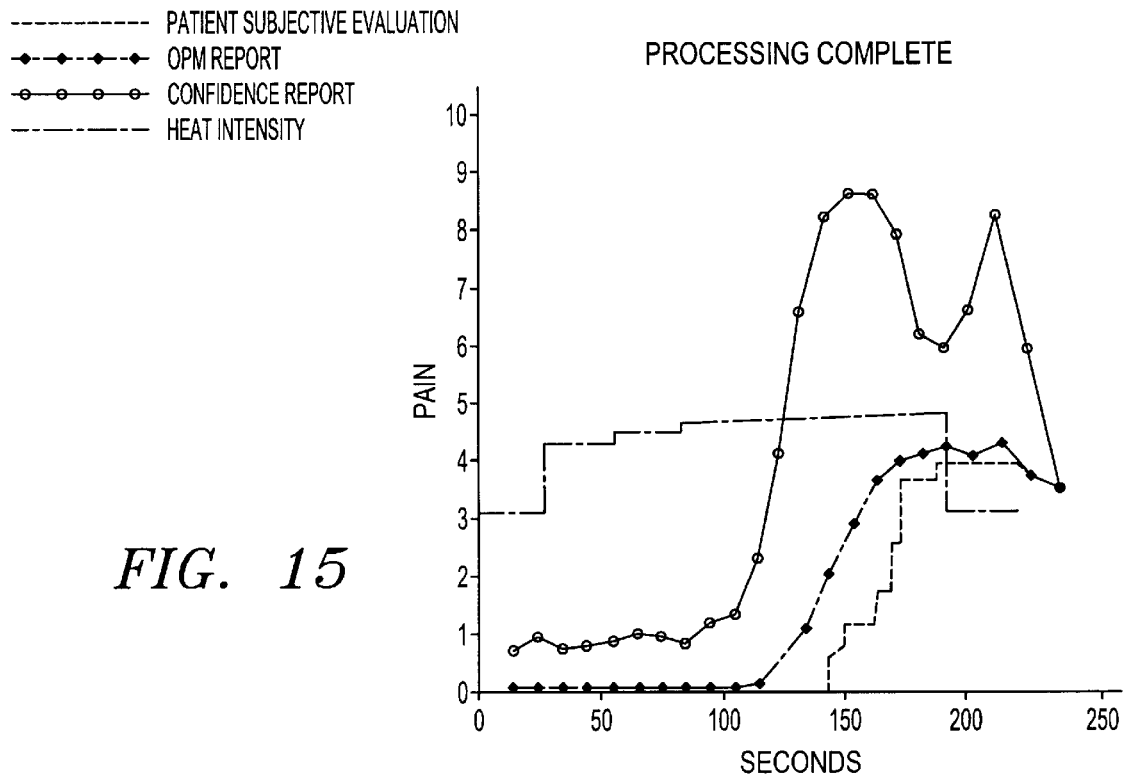
FIG. 15 is a graph depicting a first example of a typical result comparing objective pain level monitoring versus subjective pain reporting. The graph demonstrates a correlation between the subjective report and the objective reading.
Figure 16:
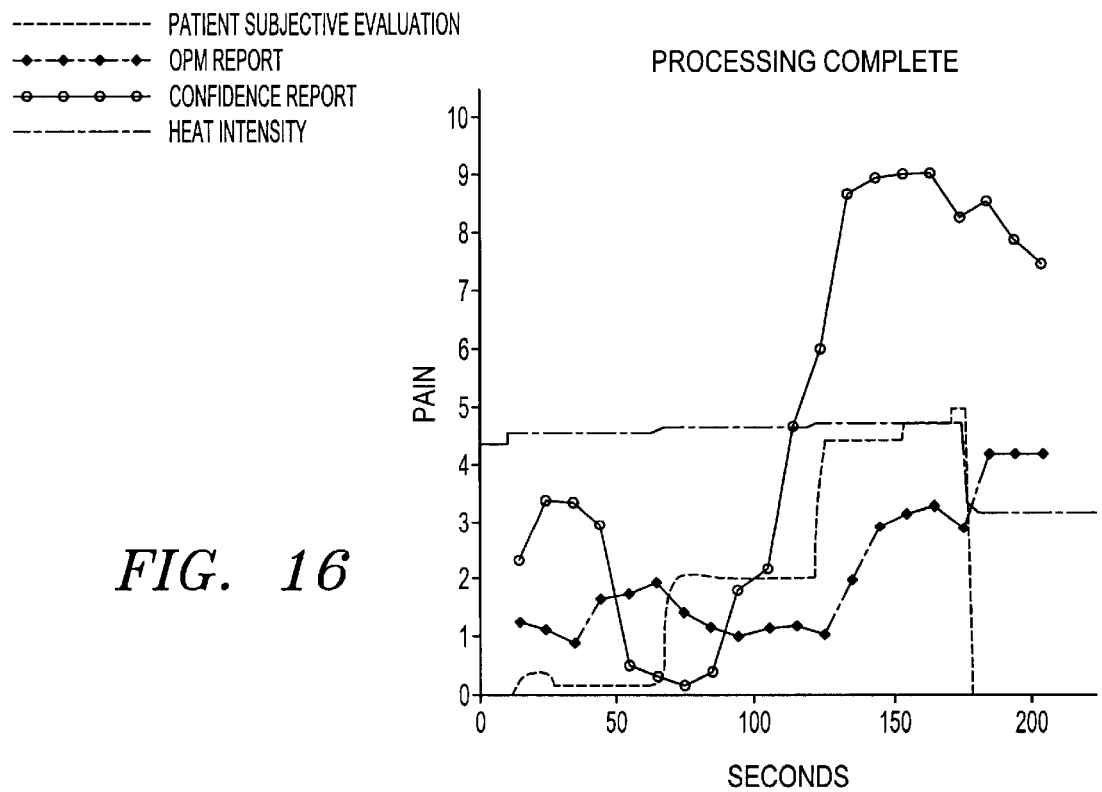
FIG. 16 is a graph depicting a second example comparing objective pain level monitoring with subjective reporting, thereby clarifying the benefit of using confidence information for rejection of artifactual pain readings.

FIGS. 15 and 16 are graphs presenting heat stimulus intensity in dashed line. The temperature in celsius is divided by 10 in order to fit the pain scale. The patient's subjective evaluation is represented by a dotted line, the objective pain level measurement provided by the OPM system 5 is represented by an asterisk-dashed line, and the confidence curve, based on $\eta_{cor}$ only, is represented by a circle-solid line. FIG. 15 depicts a first example of a typical result of objective pain level monitoring versus subjective report. This example demonstrates the high correlation between the subjective report and the objective reading. FIG. 16 depicts a second example that clarifies the benefit of using the confidence information for rejection of artifactual pain readings. The confidence curve provides a clear indication that the initial pain reading is artifactual due to movement artifacts (note the low confidence), while the second pain interval is indeed indicative of pain (note high confidence).

Figure 17:
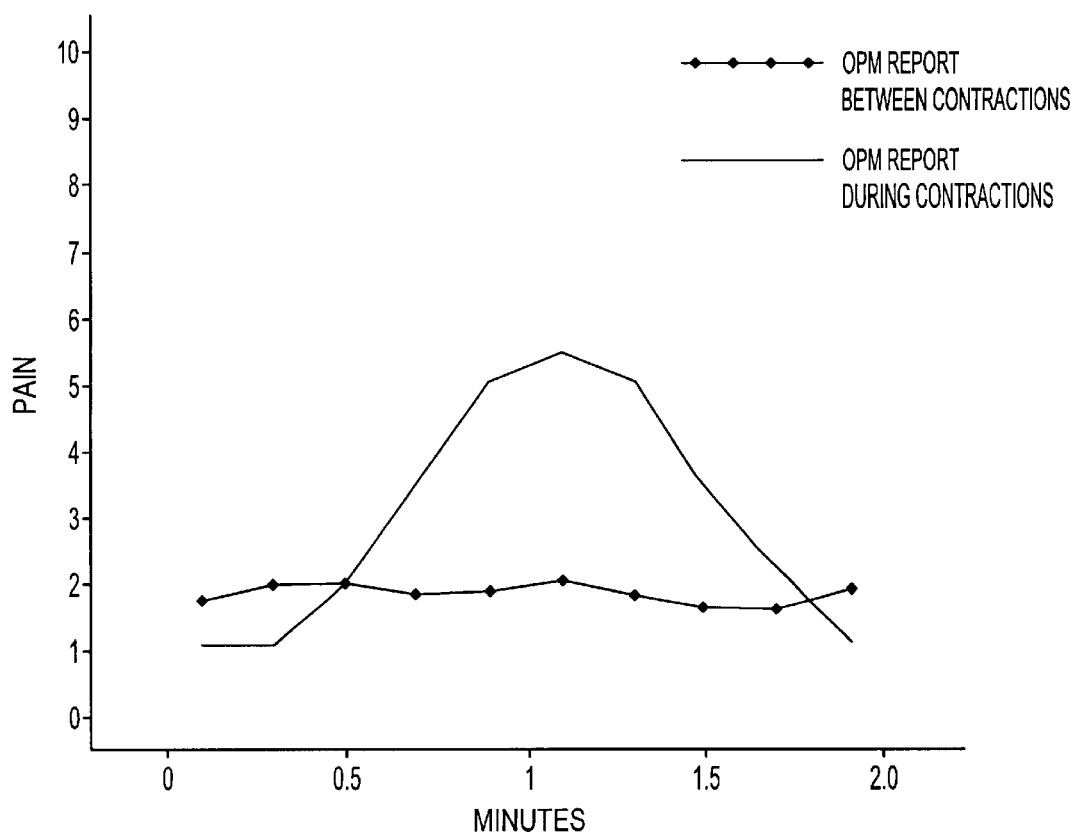
FIG. 17 is a graph illustrating pain level during labor between contractions and the progression of pain during a uterine contraction, starting with baseline level, rising to peak value at contraction climax, and returning to baseline level with relaxation.

In a second study, the OPM system 5 was tested in a clinical setting on subjects in child labor. FIG. 17 illustrates an objective pain level between contractions (asterisk-solid), and the progression of pain during a uterine contraction (solid), starting with baseline level, rising to peak value at contraction climax, and returning to baseline level when the subject relaxed.

In a third study, a subject population of healthy male and female adult volunteers, each with uneventful past medical histories, was gathered. Specifically, the subjects were considered to be free of any skin abnormality or eruption (either recent or chronic), and to be unexposed to drugs or medications that affect the central nervous system.

The Quantitative Sensory Testing (QST) model was used for the pain study. Using the Medoc TSA 2001 device, pain was induced by applying a metal plate to the skin (at the thenar emminence of the palm) of each subject. The plate was heated according to a predetermined protocol, such that pain of different levels was experienced. It is well established that beyond a certain threshold (for most subjects between 44° C. and 45° C.), the sensation of heat turns into a sensation of pain. The testing system allowed the subjects to report their subjective experience of pain magnitude by using a computerized visual analog scale (CoVAS) that was then synchronized with the signal acquisition subsystem 10 such that the temporal correlation between subjective and objective reports could be assessed.

Figure 18:
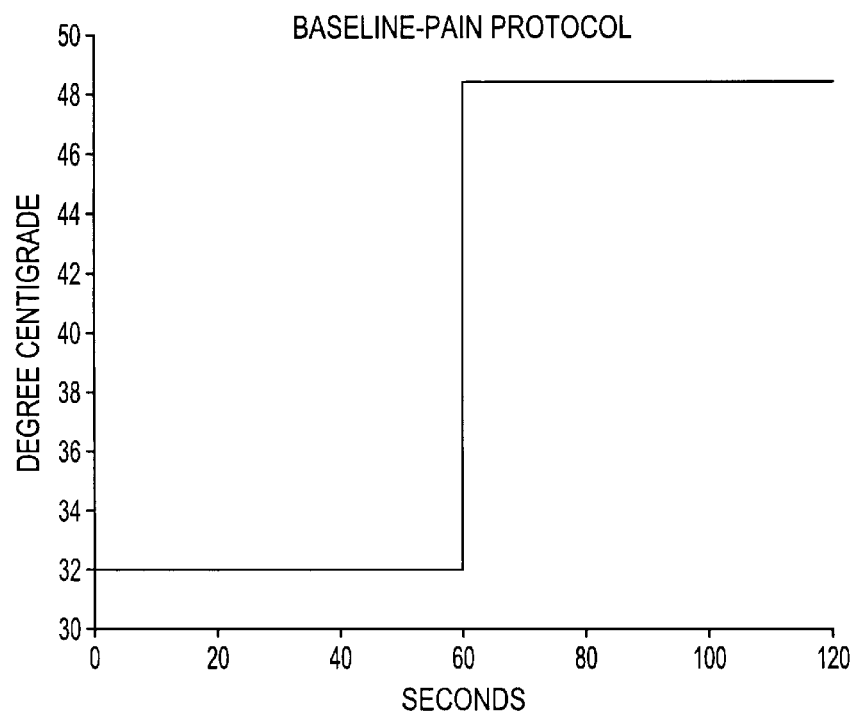
FIG. 18 is a diagram graphically depicting a first protocol (Baseline-Pain) for a study of the performance of an Objective Pain Measurement (OPM) system on a set of subjects.
Figure 19:
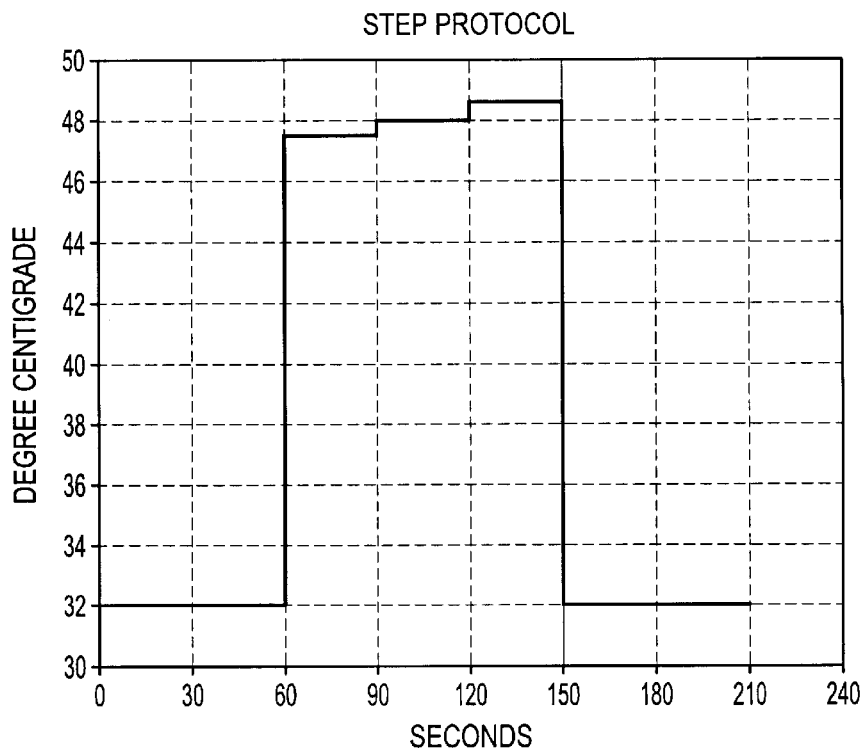
FIG. 19 is a diagram graphically depicting a second protocol (Step) for a study of the performance of an Objective Pain Measurement (OPM) system on a set of subjects.

Two protocols were designed for Quantitative Sensory Testing with the Medoc TSA2001 unit. The first was a Baseline-Pain protocol including a baseline period of 60 seconds (32° C.) followed by a painful period of another 60 seconds (48.3° C.), as shown in FIG. 18. The second protocol was a Step protocol in which the subject was exposed for 60 seconds to a baseline stimulus (32° C.) followed by three 30-second cycles of increasing heat levels, namely 47.5° C., 48.0° C., and 48.5° C., and concluded with a 60 second return-to-baseline period, as depicted in FIG. 19.

The Baseline-Pain protocol was applied to 55 healthy subjects. The Step protocol was applied to over 100 healthy subjects, nearly evenly divided between men and women, and all aged between 18–55 years.

The testing setup included a computer-controlled TSA2001 device, a Computerized Visual Analog Scale (CoVAS), and a second computer attached to amplification hardware (NORAV 1200S) for data acquisition and storage. The stored data included three streams of data, namely (a) a continuous record of the subjective CoVAS readings, (b) a continuous record of the applied heat intensities, and (c) a continuous record of the bi-channel amplified bio signals.

Testing was performed according to the following procedure:

1. All subjects received a detailed explanation of the test protocol and signed an informed consent form;
2. The subjects were seated comfortably for at least five minutes before start of the protocol;
3. The forehead sensor array was applied, the system started and signal quality was assured;
4. The subjects were asked to confirm their state of comfort and to evaluate their stress level;
5. The metal plate of the Medoc TSA 2001 was firmly attached to the right thenar emminence;
6. The subject was instructed how to use the CoVAS pain reporting system;
7. The experimental pain protocol was activated, and the CoVAS pain reported;
8. Immediately after completion of the protocol, each subject was additionally asked to describe the pain on a numerical pain scale (NPS), a categorical pain scale (mild, moderate, severe) and to draw a mark on a 10 cm analog scale (VAS). In addition, subjects were asked to describe the level of stress experienced during the test; and
9. If at any time a subject expressed severe discomfort, the subject was allowed to discontinue the procedure.

Generally, three classes of responses were obtained: Class I, comprising responses presenting high correlation between the objective reading and the subjective report (~60%); Class II, comprising responses that were not significantly correlated with the subjective report (~30%); and Class III, comprising "non-responders" (~10%). The distinction between the three types of responses is evident in the dynamic pain profiles, while average analysis for pain "spot-check" combines Classes I & II yielding a total performance approaching 90%.

The results of the "Baseline-Pain" statistical protocol were evaluated using an averaged "spot-check" reading, in order to provide a mechanism for a unidimensional, simple performance analysis. A reading of 0.7 or lower indicates no pain, 0.7–1.3 represents an inconclusive region, and a reading above 1.3 is considered as a true pain reading. The following table summarizes the statistical results obtained using the "Baseline-Pain" protocol. The inconclusive column represents borderline pain readings.

|  | CoVAS Average | PainGauge Average | True Positive | False Negative | True Negative | False Positive | In-conclusive |
|---|---|---|---|---|---|---|---|
| Baseline | 0 | 0.44 | — | — | 92% | 6% | 2% |
| Pain | 5.12 | 4.79 | 88% | 8% | — | — | 4% |

Figure 20:
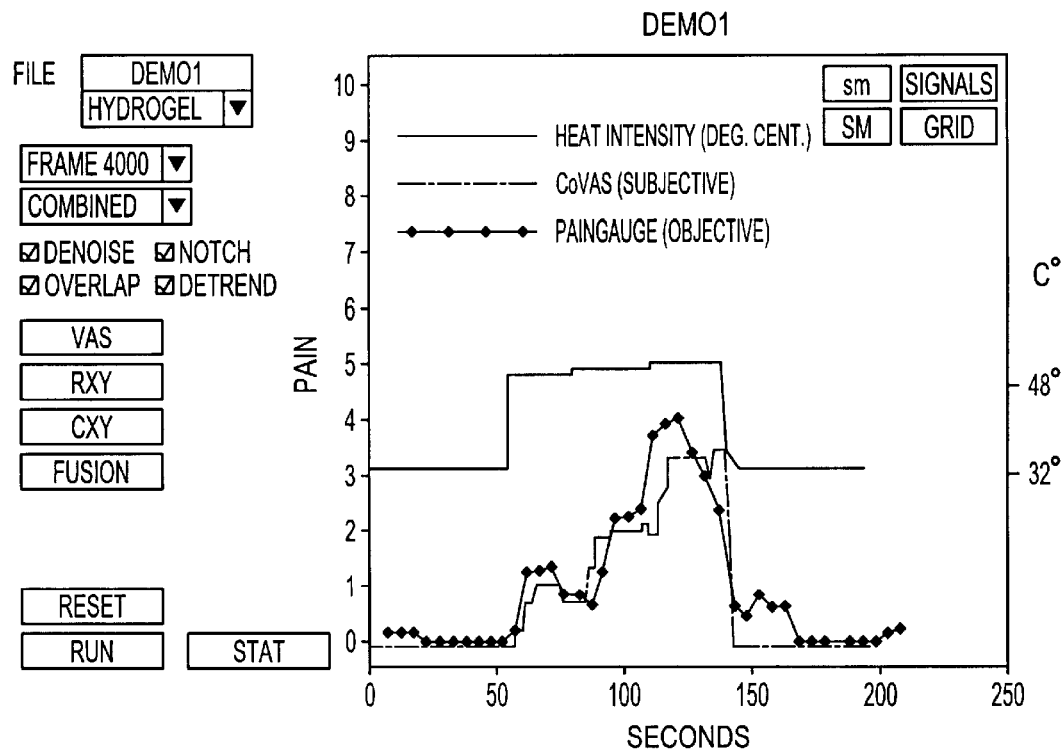
FIG. 20 is a graph depicting a typical result of applying the second protocol (Step) as depicted in FIG. 19, to a subject in an experimental study of OPM system performance.
Figure 21:
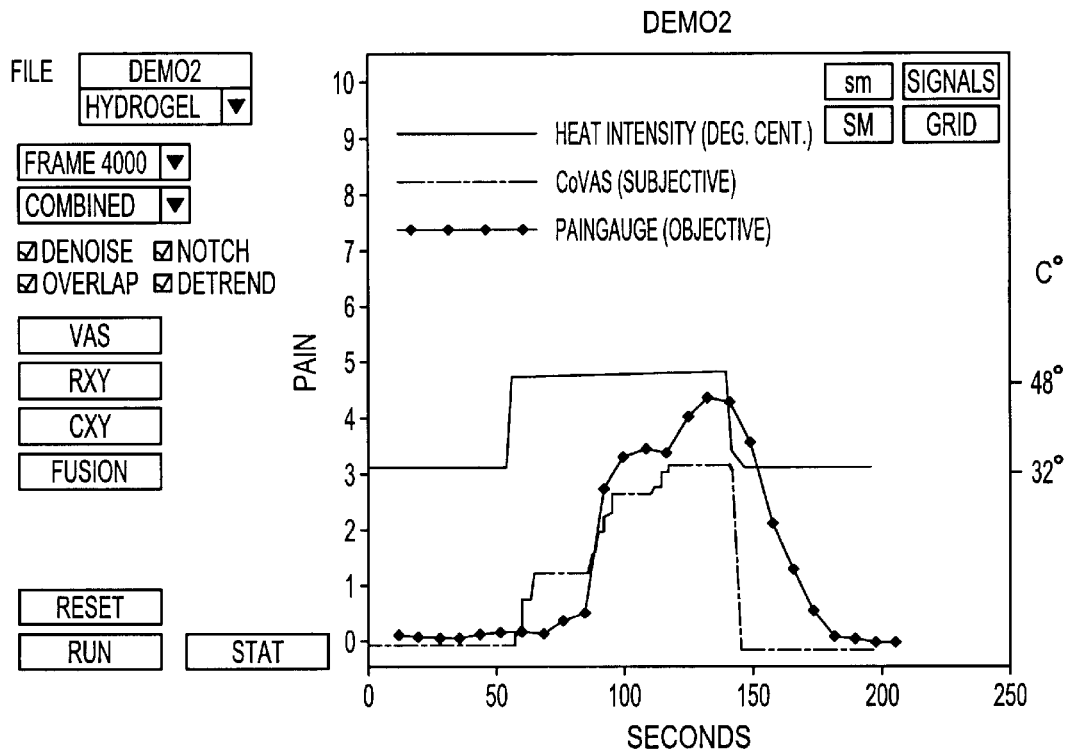
FIG. 21 is a graph depicting a result of applying the second protocol (Step) as depicted in FIG. 19, to a high pain threshold subject in an experimental study of OPM system performance.

Typical results of applying the Step protocol are depicted in the graphs of FIGS. 20 and 21. FIG. 20 presents high temporal correlation between the subjective report (CoVAS) and the objective pain curve, detecting even the very mild pain sensation of ~1 during exposure to the first heat cycle. FIG. 21 presents another case where a very mild pain cycle is not detected due to the high pain threshold of the subject.

Statistical analysis revealed significant success rates of pain detection. The Step protocol yielded substantial correlation between the subjective and objective pain curves, exhibiting fine-detailed identification of even minute changes of the pain sensation reflected in the subjective pain curves. These initial findings, although obtained from small-scale studies, indicate that the OPM system 5 performs objective detection and quantification of pain sensation.

Thus, one specific method of processing a CNS-generated composite signal to measure a subject's pain level may include any subset of the following steps:

(a) Application of a unique sensor array to the subject's forehead;
(b) Acquisition and digitization of bioelectrical signals via a sensor array;
(c) Separation of the bioelectrical signals to fCNS and sCNS components;
(d) Linear prediction analysis of the sCNS signals;
(e) Transformation of the prediction coefficients of the sCNS signals to frequency domain signals;
(f) Quantitative analysis and scaling of the frequency domain signals yielding an initial pain level score;
(g) Correlation and/or coherence analysis of composite fCNS-sCNS signals;
(h) Derivation of correlation and/or coherence coefficients from the correlation analysis;
(i) Transformation of the correlation and/or coherence coefficient(s) to confidence coefficient(s); and
(j) Integration of the initial pain level score and the confidence coefficient(s) into a final pain level reading.

In another application of the OPM system 5, the pain monitoring methods, apparatuses and systems as described herein may be used to provide closed-loop analgesia applications to patients. In one embodiment, a system and method are provided for an individualized and automated delivery of a patient's pain medication (i.e., a closed-loop analgesia system) that comprises objective CNS-based pain monitoring methods and apparatuses that use bio-electric signals.

In a separate embodiment, a drug delivery apparatus is integrated with an OPM system 5 that monitors pain levels (such as thorough CNS biosignal measurement) in order to control the amount of analgesia or other medication administered to a patient. The closed-loop analgesia system may automatically monitor the pain level and/or automatically adjust the amount of medication delivered to the patient.

Such a closed-loop analgesia/pain monitoring system may use any number of pain medication delivery methods, including intravenous delivery, epidural delivery, parenteral delivery, intramuscular delivery, intra-articular delivery (e.g. during surgery) and nasal delivery. The medication delivery methods may employ delivery devices and delivery controllers suitable to their respective methods of delivery. The system may also employ a variety of pain medications, alone or in efficacious combinations, including morphine, buprenorphine, piritramide, remifenanil, and local anesthetics, or neurostimulation devices, such as TENS.

Figure 22:
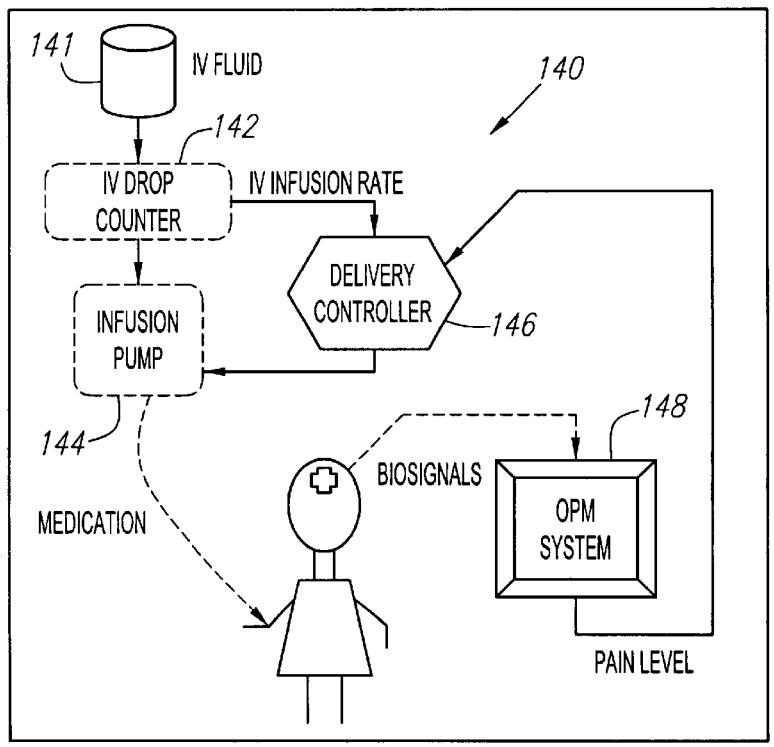
FIG. 22 is a diagram illustrating a preferred embodiment of a pain-monitored, closed-loop analgesia system employing an OPM system, such as is illustrated generally in FIG. 1.

By way of example, FIG. 22 shows a pain-monitored, closed-loop analgesia system 140 comprising an intravenous (IV) fluid container 141, an IV drop counter 142, an intravenous infusion pump 144 for a delivery device, a pump controller for a delivery controller 146, and an OPM system 148. The IV fluid container 141 is connected by a tube to the IV drop counter 142, which measures the delivery of medication. The drop counter 142 is similarly connected by a tube to the infusion pump 144, which delivers the medication to the patient. The drop counter 142 also communicates with the delivery controller, preferably through an electrical connection and preferably frequently providing the drop count to the delivery controller 146. The infusion pump provides the IV medication and, along with the OPM system 148, is connected to the patient. The OPM system 148 also communicates with the delivery controller 146, preferably via an electrical connection.

In order to regulate patient pain, the controller 146 automatically adjusts the medication amount by controlling the infusion pump 144 based on changes in patient pain level (as measured by the pain measuring device). As with most drug delivery devices, the infusion pump 144 may provide either continuous or periodic medication as desired. The medication may be provided in the form of boluses.

In other embodiments, a system for closed-loop pain controlled analgesia may include any combination or subset of the following: (a) an OPM system; (b) an IV fluid container; (c) an IV drop counter; (d) an infusion pump (a type of delivery device); and (e) a pump controller (a type of delivery controller).

In a preferred embodiment, the pain-monitored, closed-loop analgesia system 140 employs a method and apparatus for bio-signal monitoring, optionally including CNS-signal monitoring, wherein a pump controller is connected in a signal-feedback loop with a pain measuring device, an infusion pump, and a patient. However, other forms of controllers may be used, along with other drug delivery methods and mechanisms. In a preferred embodiment, the system includes a pain measuring device that measures CNS signals from a patient's forehead, such as through the use of electrodes. The signals are then used in a signal feed back loop to control a pain medication delivery device through the use of a controller.

In another preferred embodiment, the system may employ an override for nausea, respiratory depression, hypoxia, and dizziness, whereby the patient or caregiver can moderate the dose of pain medication based on these indications. Furthermore, the system can automatically monitor the patient for these override factors, including hypoxia and respiratory depression. Optionally, the system may also automatically adjust the patient's dosage of pain medication based on the detection of an override factor.

According to yet another preferred embodiment, a method of objective pain monitoring is based on central nervous system signal analysis. The analysis is carried out on short data segments reducing the effects of signal nonstationarities. The proposed algorithms provide a window into the central nervous system where different kinds of pain sensations may be evaluated and monitored. The data resulting from the algorithm may then be used to control the delivery of a pain medication to the patient.

In another preferred embodiment, an apparatus enables replacement of the patient's role in actively controlling the amount of administered medication by automatically detecting the patient's pain level and automatically delivering the appropriate amount of analgesic.

While preferred embodiments of the invention have been described herein, and are further explained in the accompanying materials, many variations are possible which remain within the concept and scope of the invention. Such variations would become clear to one of ordinary skill in the art after inspection of the specification and the drawings. The invention therefore is not to be restricted except within the spirit and scope of any appended claims.

What is claimed is:

1. A system for delivering medication for reducing pain in a subject comprising:

(a) a reservoir for containing the medication;

(b) a delivery device connected to the reservoir for delivering the medication to the subject;

(c) a delivery counter connected to the reservoir for measuring the medication transferred between the reservoir and the delivery device;

(d) an objective pain measurement device for objectively measuring a subjective perception of the pain in the subject;

(e) a medication delivery controller in communication with the objective pain measurement device, the delivery counter and the delivery device for controlling the amount of medication delivered to the subject by the delivery device based on a delivery rate communicated by the delivery counter and an objective pain measurement communicated by the objective pain measurement device.

2. The system of claim 1, further comprising an override device, electrically connected to the delivery controller for modifying the delivery of medication to the patient based on override factors detected from the patient.

3. The system of claim 1, wherein the reservoir is an IV fluid container, the delivery device is an infusion pump, the delivery controller is a pump controller, and the delivery counter is an IV drop counter.

* * * * *